US007771442B2

(12) United States Patent
Shriver

(10) Patent No.: US 7,771,442 B2
(45) Date of Patent: Aug. 10, 2010

(54) GRAFT CORE FOR SEAL AND SUTURE ANASTOMOSES WITH DEVICES AND METHODS FOR PERCUTANEOUS INTRALUMINAL EXCISIONAL SURGERY (PIES)

(76) Inventor: Edgar Louis Shriver, 3600 Mystic Pointe Dr., Apt 1715, Aventura, FL (US) 33180

( * ) Notice: Subject to any disclaimer, the term of this patent is extended or adjusted under 35 U.S.C. 154(b) by 1595 days.

(21) Appl. No.: 10/994,102

(22) Filed: Nov. 22, 2004

(65) Prior Publication Data
US 2006/0111733 A1    May 25, 2006

(51) Int. Cl.
*A61B 17/08* (2006.01)
(52) U.S. Cl. .......................................... 606/153; 606/151
(58) Field of Classification Search ............... 606/153, 606/151
See application file for complete search history.

(56) References Cited
U.S. PATENT DOCUMENTS

2001/0044631 A1   11/2001   Akin
2003/0088256 A1    5/2003   Conston
2003/0195457 A1   10/2003   LaFontaine
2004/0073238 A1    4/2004   Makower
2004/0097992 A1    5/2004   Spence
2004/0116946 A1    6/2004   Goldsteen

*Primary Examiner*—Julian W Woo
*Assistant Examiner*—Melissa Ryckman

(57) ABSTRACT

The present invention is a combination anastomosis device that both sutures and seals connections between two native body tubes and a graft—better proof against leaks than prior art of suturing alone or as some propose, by sealing. The invention is also a combination of supporting devices and methods that allow the anastomoses to be performed in seconds rather than the minutes required by present art, causing no more collateral bodily damage than percutaneous entry, requiring no time on a cardiac bypass system, either no heart stoppage or less than a minute thus potentially increasing the population who can tolerate coronary bypass as an out-patient procedure. The tract of application is not limited to coronary but includes vascular, urinary, pulmonary, alimentary, cerebral-spinal or other mammalian tract. May be manufactured of biodegradeable or biocompatible material and graft may be harvested or synthetic.

10 Claims, 18 Drawing Sheets

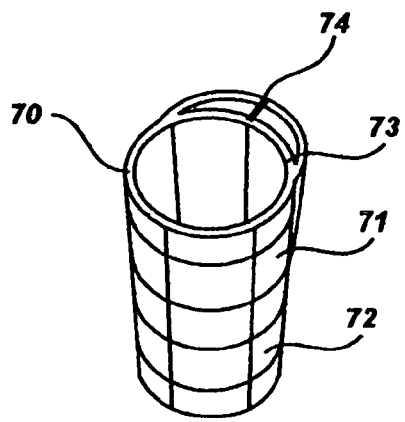
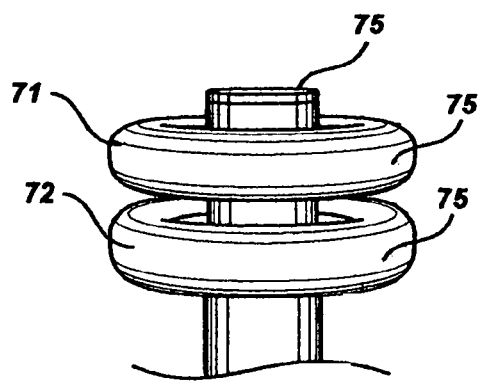
Fig. 6a  Fig. 6b
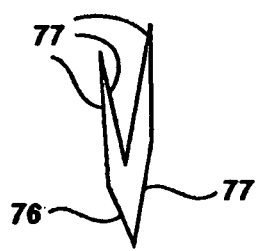
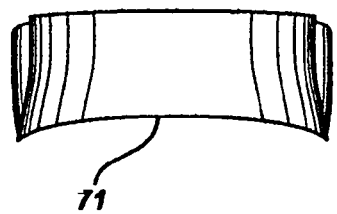
Fig. 6c  Fig. 6d

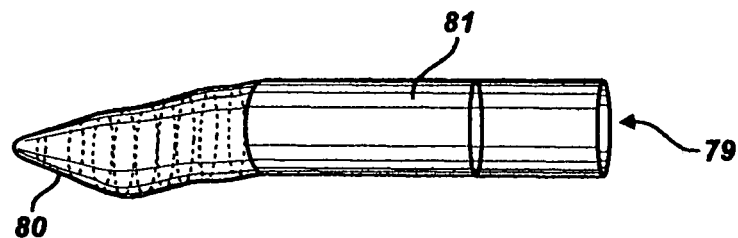
Fig. 7
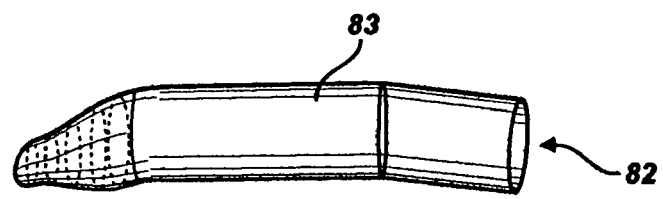
Fig. 8
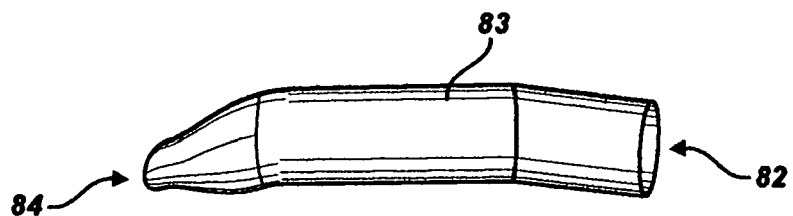
Fig. 9a
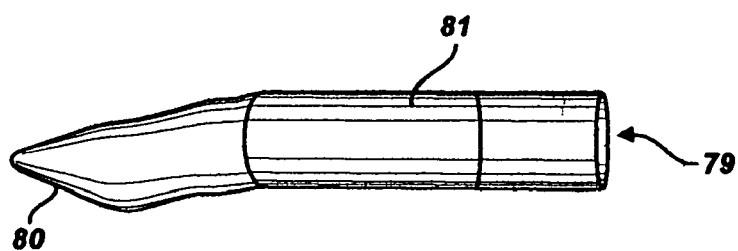

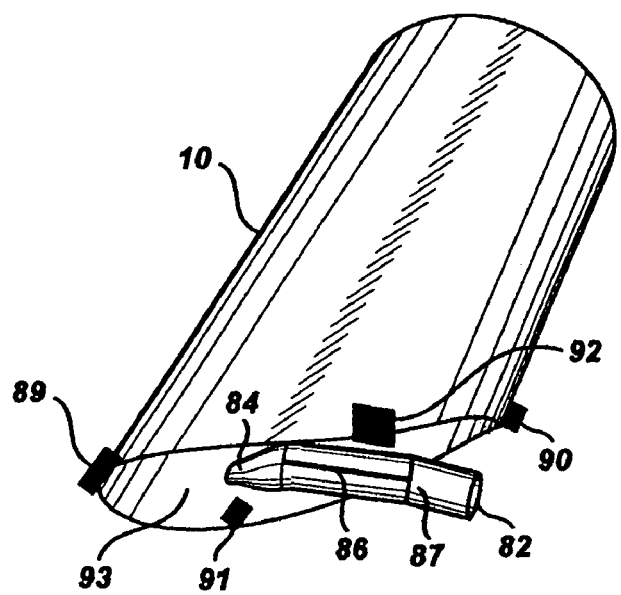
Fig. 9d
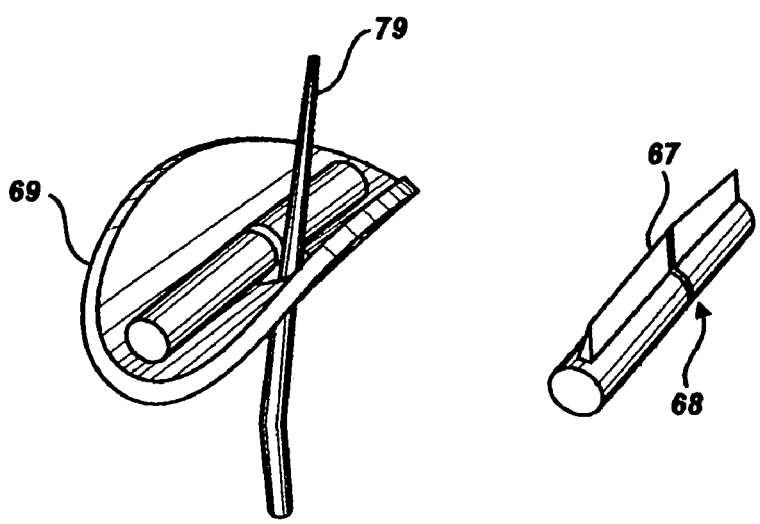
Fig. 10a          Fig. 10b

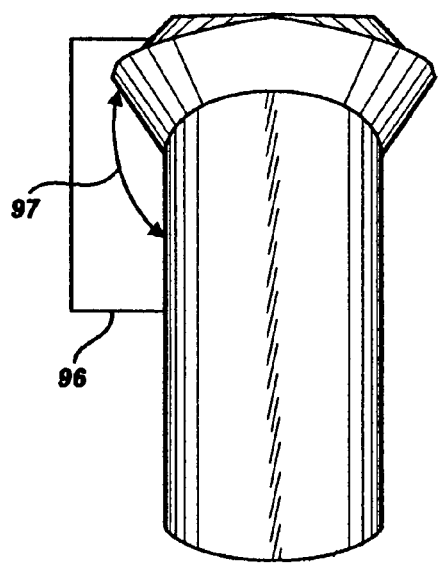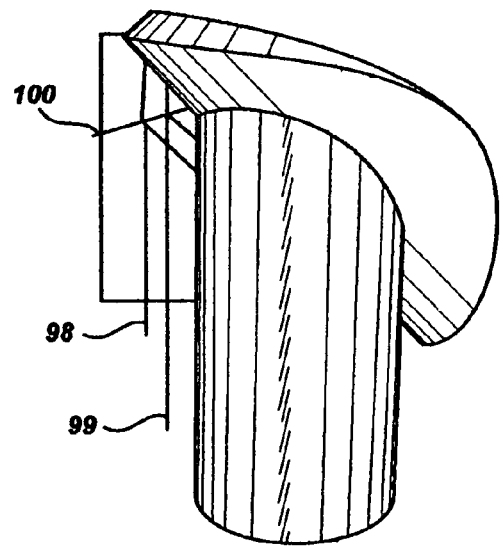
Fig. 12c        Fig. 12d

GRAFT CORE FOR SEAL AND SUTURE ANASTOMOSES WITH DEVICES AND METHODS FOR PERCUTANEOUS INTRALUMINAL EXCISIONAL SURGERY (PIES)

BACKGROUND OF THE INVENTION

Wounds of battle created a need for surgeons. The point of body entry was the choice of battle, not the surgeon. The devices were the knife, saw, clamp, needle and thread. The methods and skills for using the tools were not much different than those of the ship's carpenter or sailmaker. The term "surgery" made no distinction between collateral damage and damage necessary to effect the desired bodily change and that remains essentially true today. Skill with new devices, methods and pharmaceuticals have improved, making elective surgery feasible.

A substantial percentage of elective surgical procedures involve joining or anastomizing tubes that are not joined naturally. This is because there are a large number of tubes carrying essential body fluids for circulation and excretion and they often suffer physiological damage. Such sites in tubes are frequently by-passed with another tube extracted from the body or made of artificial material. A few examples illustrate the variety, e.g., urethras for gastrointestinal disorders, blocked arteries, shunts for dialysis, cerebral spinal shunts and bypasses of scarred fallopian tubes.

In common medical usage the term "anastomosis" is used for joining or grafting two tubular body parts that are conduits for a fluid. The term is derived from the Greek, referring to opening a mouth, originally referring to the mouths of river branches but used by early anatomists for branching tubular body parts including blood vessels and nerves. The terms "side-to-side" and "end-to-side" are used to distinguish between anastomoses that directly join the cut sides of two tubes and those where the transected end of a tube, called a graft is joined to the artificial opening in the side of another tube. The graft is generally described as a body portion with a first end, a second end and a lumen therebetween. The term "lumen" refers to the inside of the tube where some substance flows. Body tubes are also called conduits or vessels. Since conduits can be troughs and vessels can be objects floating through conduits the term "tube" is used here.

Disease in coronary arteries is the leading cause of premature death in industrialized societies. This makes the importance of anastomizing tubes in a coronary bypass so great that surgical methods involving extreme collateral trauma and risk to the patient are justified. In coronary artery bypass graft CABG, surgeons cut, crack and saw their way through the chest to get their hands in place for making anastomoses, which are the necessary to connect coronary arteries distal to the point of narrowing to a blood supply from the aorta. MIDCABG procedures are endoscopic and involve less collateral damage but still represent a severe strain on patients and have replaced CABG procedures in only a small percentage of cases. CABG will remain the gold standard until more compelling alternatives than MIDCABG are found. Anastomoses of coronary arteries are challenging because they are tiny, friable, intolerant of injury and moving with each beat of the heart. The manual skills for sewing extremely small sutures in tiny frail tubes are well perfected by those who perform CABG surgeries but each anastomosis represents a chance for error or stress beyond what the patient can tolerate. To enable these anastomoses to be done at all the heart must be stopped and circulation placed on an artificial bypass machine so the surgeon does not have the added complications of a moving target in a bloody field. This represents further collateral damage. The risk in heart stoppage is always high, but goes up sharply if time on bypass machine lasts longer than an hour. Suturing by hand takes about ten minutes at each site and in a triple bypass operation six sites require an hour. Sometimes the suturing is inadvertently loose, allowing fluid to leak which can cause acute or chronic loss of blood pressure and possible scarring which results in another blockage. In addition to the threat of leakage, fluid mechanics are such that introducing a stream into a tube at a substantially different angle or velocity of flow than is normal for the tube can cause damage. There is a constant search for improved devices and methods for making anastomoses to reduce the possibility of leakage and time on bypass machine.

This search for alternatives has led in two directions, the first to improve the CABG procedure, the second to eliminate it. The first centers on devices inserted in tubes during MIDCABG or CABG procedures to accomplish anastomoses faster and better than suturing thus reducing or eliminating time on the bypass machine, duration of heart stoppage and leakage. There are metal devices and those that look like plumbing fixtures to make anastomoses faster and/or better. The only ones of relevance to the present invention are those that use seals as they can be advanced intraluminally after percutaneous entry. The alternatives for eliminating MIDCABG and CABG procedures involve use of devices and methods originally developed for percutaneous coronary intervention (PCI).

Three inventions involving seals but intended for use in CABG and MIDCABG procedures are summarized here. One device by Akin, Conston, et al in US Patent Application 2001/0044631, consists of two flexible sheets of material of any shape connected around the circumference of an opening near their center, deployed through openings in side-by-side lumens and held by fluid pressure in each tube. It is claimed this seal is more fluid-tight and more quickly installed by the surgeon's hands than is suturing. Their tests conducted on swine tend to bear this out. However, in the event that a seal alone is not so leak-proof as hoped, the claims include an embodiment where adhesive is used for a tighter seal. An associated device, described as a surgical dispenser, is used to hold the compressed flexible sheet as it is manually inserted through the side of body tubes. Akin, Conston, et al in US Patent Application 2003/0088256 A1, describe a similar seal partially held in place by fluid pressure but aided by various configurations of support members deployed inside each lumen and in the opening between them. Again adhesives are included in one embodiment. This device is manually inserted through the side of tubes though an end-to-side version is mentioned with a figure but it is not included in their claims. In a third invention, Spence, et al, in US Patent Application 2004/0097992 A1, claims a device of two flexible vessel attaching segments called "double cuffs," connected around the opening between them and placed in the lumens of side-by-side tubes where fluid pressure temporarily holds them in place. With this device there is no doubt regarding the temporary nature of this seal because an oval of malleable studded metal segments surrounds the opening in each tube and is attached to the flexible seal. These clamps are pressed through the opening and into the metal oval opposite to accomplish a permanent connection. In these three devices it has not been proven that they are more leak-proof than manually applied sutures but, at the very least they suggest the value of seals. Further it is evident that these devices can be emplaced in less time than the approximately ten minutes it takes to manually suture an anastomosis. Though they appear to have certain advantages over manual suturing, they are limited to CABG and MIDCABG operations.

In the present invention an end-to-side seal is used, temporarily held in place in one tube by fluid pressure, but made permanent by sutures drawing it against the lumen. As a permanent seal it represents one of two methods used to make the anastomosis leak proof. The other is non-manual suturing of the same anastomosis. This combination of seal and suture in the present invention must be better proof against leaks than suture alone or seal alone. Because it requires only seconds to emplace, it provides the advantages of no time on bypass machine and either no heart stoppage or less than a minute. In addition the present invention includes a combination of devices for conducting the necessary operations intraluminally after percutaneous entry thus avoiding all the collateral damage of CABG and MIDCABG procedures.

Long catheters and fluoroscopic devices make it possible to select a point of entry far from the targeted coronary artery. This is called a percutaneous method in the sense that only skin is broken. The site for entry is chosen where there are no interposing body parts between the skin and the tube. Originally the devices and methods introduced at sites in the groin or arm were for the purpose of advancing and inflating a balloon at a narrowing in a coronary artery. Later a stent device was added, now a chemical eluting stent is used to inhibit growth. Each device was an improved invention for intervening at a narrowed, or otherwise damaged, arterial site. The successive devices were invented and patented while the general method continued to be called Percutaneous Coronary Intervention (PCI) and it's practitioners, interventionists. These methods essentially avoid all collateral damage. Catheters were not originally intended to be used for surgical entry to the body. However with appropriate devices and methods they can be. Several inventions, including the present one do so. This represents the ultimate reversal of entry to the surgical field which was originally determined by battle. It also represents a clear distinction between collateral and necessary damage in surgery.

An example of percutaneous and intraluminal entry to the surgical field is found in an invention by Makower in US 2004/0073238, Device, System and Method for Interstitial Transvascular Intervention. It describes an invention for percutaneous entry, intraluminal advancement to a desired location, opening of an artificial port to another blood vessel or organ, tumor or other anatomical structure so that one or more operative devices can be advanced to perform the desired procedure. Several inventions share this object and method, including the present one. Indeed this description represents the longer highway to the surgical field that is the new alternative to the direct road created by battle damage or surgical bulldozing. If each of the highways had been patented by the early anatomist who discovered it, said patents would have lapsed centuries ago. It remains to be seen what devices are devised to travel this road and for what objects. The need for tracking devices is common to catheter-based systems, e.g. fluoroscopic, and those that leave the highways of natural body tracts to venture outside the tracts are likely to need even better tracking devices. Makower describes active and passive orientation detection by means configured of any of a known set of materials that would allow for the radiographic, fluoroscopic magnetic, sonographic or electromagnetic detection of the location of devices in the body. Use of these various known forms of energy for localization is obvious. Two of Makower's objects make it clear how his invention is different from the present one. One object is the use of a coronary vein running parallel to the coronary artery as a bypass conduit while terminating the vein's original purpose as a vein. He terms the tiny space between tubes as interstitial, while transluminal refers to going across the parallel tube lumens. The means of joining is side-to-side. The present invention utilizes the CABG method of a harvested vein graft to bypass the occlusion with its proximal end starting at the aorta and distal end at the coronary artery with both anastomoses end-to-side. Though the overall object of revascularization is the same and both inventions use catheters to advance on similar highways with localization by the usual sources of energy before and after leaving the highway, the intermediate objects, devices and methods for achieving them are quite different. A second object of Makower's device is transmyocardial revascularization which involves evacuating a channel of tissue between vein and left ventricle. This seems as promising as his other method though both may have their own disadvantages. Regardless of potential advantages and disadvantages, these methods for revascularization are quite different from the method of this invention and certain others that involve a graft between aorta and coronary artery. Makower claims applicability to tracts in the mammalian body other than vascular and that the vascular tract is merely a conduit to other fields of surgery. The present invention and others based on percutaneous entry and transluminal advancement of devices make similar claims about generality.

There is a need for devices and methods that achieve revascularization by the method of coronary bypass proven in millions of CABG procedures but with percutaneous entry, intraluminal advancement, cutting tubes for optimal joining of epithelial layers, clamping, delivery of graft, leak-proof anastomosis done without manual manipulation and quickly enough to avoid bypass machine circulation entirely, with little or no heart stoppage and without the trauma and risk of collateral damage. Fulfillment of this need for patients who cannot tolerate more invasive surgical procedures but can tolerate excisional intraluminal surgery would represent a benefit to a far larger population than the 500,000 or so who now tolerate CABG procedures each year.

Two inventions are described below that involve percutaneous entry, transluminal advancement of devices, cutting openings, clamping openings, tracking devices energized by various but obvious alternative forms of electro, magnetic, mechanical energy, snaring guidewires to lead from aorta to artery and use of wire mesh and stents to make anastomoses with the aid of balloons. These inventions and the present invention use the bypass graft common to CABG as a means of illustrating their preferred embodiments but claim greater generality. The present invention does not leave wire or stents in the body but can utilize biocompatible material if there is no desire to use biodegradable material which is absorbed after the anastomosis heals.

Goldsteen, et al in Medical Grafting Methods and Apparatus, US Patent Application 2004/0116946 A1, and LaFontaine, et al in System and Methods for Percutaneous Coronary Artery, US Patent Application 2003/0195457 make claims that are similar, including some that are similar to the present invention. Both the inventions cited describe a method of connecting the aorta and coronary artery target site by a single continuous guidewire. Both use a snare method to accomplish this but Goldsteen describes a device placed in the coronary artery to deflect the guidewire through the wall. Both snare this wire by a loop of guidewire pushed through the wall of the aorta and substitute one continuous wire for the snared pair. Goldsteen utilizes endoscopic fiber optic light to illuminate and view the snare. Both advance a guiding catheter to an exit site in the aorta. Both advance a sharpened guidewire or stylet through the catheter to cut through the aorta wall. Goldsteen enlarges this opening by twisting a threaded conical tip hoping that this may facilitate transfer of macerated, loosened tissues into a larger proximal catheter. Successively larger catheters are twisted and pushed though the opening until the largest, the guiding catheter is pushed through. This guiding catheter has a pair of annular balloons that are inflated on either side of the opening to clamp it. It appears from the figures that the inflation lumens for these balloons are coincident with the catheter wall and if so, that would need correction or explanation. There is no requirement to stop the heart. LaFontaine has one embodiment where the heart is stopped and another where it is not while he utilizes a vacuum device to isolate and stop blood flow before cutting through the aortic wall. No indication is provided about the size of cut but after it is made the everted graft mounted on a coupler is pushed (bare) through the opening where it is reverted to outside out as it travels though the pericardium on the wire between aorta and artery. Several electro, magnetic, mechanical devises in addition to radiopaque markers for tracking and locating the graft end are described. Goldsteen utilizes radiopaque markers and orthogonal fluorescent screens to track and display location of an artificial graft conduit as it moves mounted on the outside of a catheter through the pericardium on the guidewire. The artificial conduit is a stent-like wire mesh with interstices filled with artificial graft material. Then one of several versions of a threaded or barbed tip cuts or grinds its way through the artery wall. The artificial graft is advanced through the opening and its wire ends spring radially inside the artery lumen. In case these do not make good contact a balloon is inflated in the opening to adjust them. This process is repeated at the opening in the aortic wall with rings of barbs on either side of the wall. If it is desired to use a natural graft instead of the artificial one, it is placed inside the artificial graft for delivery and attached after the artificial graft is attached namely to the tube walls by rings of barbs pushed on either side of each wall by balloons. In an alternative embodiment the natural graft is not preceded by the artificial graft. LaFontaine cuts an opening of unspecified dimensions in the artery wall and the reverted graft is pushed inside the artery coaxial with the artery. It might be noted that coaxial alignment leaves the epithelial layers of the graft and tube separate by the full thickness of the graft. Regardless of this, a short cylinder of wire mesh is placed either inside or outside the graft end which is expanded by a balloon to the diameter of the artery. If this is insufficient to keep it in place an alternative embodiment provides a short cylinder of adhesive to hold it. The graft is attached to the aorta in a similar manner. He describes variously shaped wire mesh, stent-like devices and balloons to push them into place to keep the graft attached to artery and aorta.

The present invention utilizes a combination seal and suture grafting device of biodegradable or biocompatible material that is not dependent on wire and glue to hold graft and tube together. It also provides that the intimal layers of graft and tube are in good contact for sure and fast growth— certainly better than is possible with coaxial contact or gross manipulations with balloons and wire mesh. This is accomplished on the graft preoperatively by a cutting template so its ends are cut to the proper angle for intimal contact with the intima of the tubes it joins. This is maintained by cutting instruments that cut openings of the correct size in tubes so as to expose their intimal linings for proper joining of graft and tube. There is no maceration of delicate tubes involved in any cutting and no irritation by repeated driving of metal barbs though their frail walls. Stiff sutures are driven through the walls in a more delicate manner than provided even by manual suturing as no needle precedes the tiny sutures. The suturing of graft is also completed preoperatively so that only the final stitching to the tubes takes place during the operation. This requires only seconds and no heart stoppage. The sole reason for possibly stopping the heart would be to hold the graft against the heart without it bouncing away and this for no more than a minute. The dual balloon clamps of the present invention do not require heart stoppage as a vacuum device might. The present invention's annular balloons clamp on either side of the aortic wall at a distance from the opening so as not to squeeze the end of open tissue in a way that later impairs the union of its intimal layer with the intimal layer of the graft. The graft in the present invention is transported inside a catheter delivery tube where it is protected from inadvertent injury during transport and it does not suffer the double insult of eversion and reversion. The present invention does not involve placing a continuous guidewire from artery to aorta as other means appear less damaging. The present invention provides two techniques for manipulating the obvious electro, magnetic, energy sources for tracking the graft and delivery tube, a delay line between electromagnetic transmitter-receivers and a variation of the century-old Wheatstone's bridge network for detecting tiny differences in electrical signal strength.

The devices, pharmaceuticals and methods for accomplishing PCI are described in numerous publications, e.g., The Interventional Cardiac Catheterization Handbook by Morton J. Kern, second edition, 2004, Mosby, Elsevier Inc. To the extent appropriate, devices, methods, pharmaceuticals and general knowledge from such sources as describe that state of the art are applicable to the present devices and methods in various application situations. Of course things that are appropriate vary with the application. For instance heparin, nitroglycerin and certain other pharmaceuticals, appropriate in a homeostatic application would not be appropriate in an application to fallopian tubes or colon. However catheters would be common to all applications.

SUMMARY OF THE INVENTION

The present invention provides a double-seal device for making leak-proof anastomoses that connect the lumens of two native body tubes through a graft. The purpose is to make anastomoses more secure than can be achieved by suturing alone or sealing alone. A combination of devices and methods support this device in achieving five other objects. First, only seconds are required to make each anastomosis rather than the minutes required for manual suturing; second, no more collateral body damage than percutaneous entry; third, little or no heart stoppage required for coronary bypass operations and no time on bypass circulation machine; fourth, applicable to any vascular, urinary, pulmonary, alimentary, cerebral-spinal or other mammalian tracts and, fifth, the possibility of increasing the population that can tolerate a needed procedure, especially if reduced to an out-patient basis. The sealing graft core and sutures are manufactured of biodegradable materials absorbed by the body after the graft is complete, unless the option of the graft being a foreign body is exercised, wherein the devices are made of non-bioresorbing material. In any case the graft device is coated with appropriate growth supporting biochemical and/or endothelial cells as well as other pharmaceuticals. The first native tube is the site of percutaneous entry or, in some tracts, entry is through a natural body opening. After initial natural or percutaneous entry and intraluminal travel, the first opening to the field of surgery is cut from inside to outside the first tube, thus percutaneous intraluminal excisional surgery (PIES).

The devices and methods which constitute the preferred embodiment of the present invention are summarized as follows. A clamping catheter with a cutting balloon is advanced transluminally from the point of entry to the site of the anastomosis in the first tube. After cutting and clamping the wall opening at this site an explorer guidewire is advanced through the opening with one or more of five forms of devices for locating the target on the second tube. When located, the tip of the guidewire is screwed in as an anchor.

A delivery catheter slidingly fitted inside the clamping catheter is advanced on the explorer guidewire to the anchored target site. It contains a previously prepared length of graft attached to graft cores at each end by hollow sutures, posts and a circular suture. The brims of the distal and proximal graft cores are slightly compressed to enter the delivery tube. The delivery catheter also contains a catheter with a rodding balloon on its end fitted inside the graft core. The delivery catheter is capped by a holding balloon on which is mounted a cutting device. This makes a slit on the longitudinal axis of the second tube. The delivery tube is immediately pushed through the opening far enough that the brim of the graft core and holding balloon are in the lumen and the stem is in the opening. To remove the graft core from the delivery tube, the rodding balloon is partially inflated to engage the base of the graft core stem. The holding balloon is pulled back and the rodding balloon advanced sufficiently to grip the graft core while the delivery catheter is withdrawn. This allows the brim to expand in the lumen of the second tube and the wall of the second tube to close around the stem of the graft core. This forms a seal as pressure inside the lumen presses the graft core brim against the wall of the lumen which has the same shape as the brim. The key on the distal end of the rodding balloon is in a keyway inside the stem which aligns each rod with the proper stiff suture. The rodding balloon is fully inflated to bring the rods in line with the stiff sutures each is assigned to drive. The stiff suture that must travel the longest distance to enter the brim is in contact with the rod that will drive it first and therefore farthest and the stiff suture with the shortest distance to travel is placed in contact last. This may be accomplished by rods of different length or by stiff sutures at different distances from the base of the graft core. Either way, the rods are advanced through the hollow cones of the hollow sutures in which the stiff sutures are lodged. With the holding balloon pulling the brim of the graft core against the lumen wall, the rodding balloon is advanced, driving the sharp ends of the stiff sutures through the wall of the second tube and into the brim. Barbs prevent the stiff sutures from backing up from this position.

This completes the distal anastomosis with both sutures and seal in place. The cutting device and holding balloon are deflated and removed but the rodding balloon is left in the delivery tube to be used again with the proximal graft core. The delivery tube is withdrawn, with the proximal graft core and rodding balloon, to the site of the clamping balloons so that the proximal brim is in the lumen of the first tube and the stem in the opening. A proximal holding balloon (a mirror image of the distal holding balloon) is advanced through the clamping catheter to a position of pushing against the brim of the proximal core. The process of aligning the key in the keyway and gripping the graft core is performed before deflating the clamping balloons and withdrawing the clamping catheter from the immediate site. The delivery tube is then removed from the site while the proximal graft core is gripped. The rodding balloon is deflated slightly and advanced sufficiently to clear the longest rod distally from the interior of the stem, then inflated to align the rods with the stiff sutures they are to drive into the brim. The holding balloon is pushed against the brim and the rods are driven to complete the second anastomosis. The graft is now sutured and sealed. The devices are withdrawn and the percutaneous entry closed in the usual manner.

The anastomoses can be on different body tubes, e.g., vein and artery for dialysis or at proximal and distal points on the same tube, e.g., loops of the colon. The first tube may have branches with different names, any one of which can be the second tube, e.g., the aorta having branches called the left, right and circumferential coronary arteries. It may be noted that the skin can be one of the tubes, as in an operation for colostomy.

The term "first tube" refers here to the first tube entered for delivery of the devices rather than the first tube to receive an anastomosis. The term "second tube" refers to the second tube entered—even if it is a distal part or branch of the same tube with the same or a different anatomical name. To further avoid confusion it is pointed out that with the present devices and methods the second tube entered is the first to receive an anastomosis.

The devices and methods revealed here utilize the two transected ends of a graft, and thus do not produce a side-to-side graft. If adjacent tubes are to be joined with the devices and methods revealed here, the graft or grafts can be cut so short that the end-to-end graft functions like a side-to-side anastomosis. It may be noted that commonly, and particularly herein, the third tube is called the graft. So the terms used here for the body parts being joined are first tube, second tube and graft. These terms are generic and exact as well as simple and direct, an advantage in a discussion as abstract as a patent application.

The devices are made of collagen or other bioresorbable material that disappears after the graft has healed (become a stoma) or biocompatible material if the graft is to remain in the body as a foreign object. The devices are imbedded with such biochemicals as will support the growth at the sites of the anastomoses. Biochemicals that promote slipperiness may also be used as adhesives. The graft is obtained by customary harvesting means, from the patient or a donor unless a foreign body is selected from one of many non-biological sources. The devices and methods are designed to be used with PCI methods, pharmaceuticals and techniques.

More specific details are provided regarding this invention's devices and methods in application to a coronary bypass because the small sizes of coronary arteries make the sizes of devices critical. It is perceived as important to show that the invention's devices that must be stacked inside each other will still fit within small coronary arteries—down to a certain limiting size. This is not intended to limit the devices of the invention to this application, but to show details that are critical with respect to any body tubes of such small size.

BRIEF DESCRIPTION OF THE DRAWINGS

FIG. 6a shows the end of a clamping catheter with deflated clamping balloons and a dual channel made by a double wall.

FIG. 6b shows the clamping balloons inflated with radiopaque markers.

FIG. 6c shows a cross-sectional view of one semi-inflated clamping balloon.

FIG. 6d shows a cross-sectional view of a deflated clamping balloon.

FIG. 7 shows the explorer guidewire with screw tip and radiopaque longitudinal marker.

FIG. 8 shows the target guidewire with longitudinal radiopaque marker.

FIG. 9a shows the explorer guidewire with transmitting tip and target guidewire with a receiver tip.

FIG. 9d shows two transmitters mounted in the target guidewire surrounded by 4 receivers on the distal opening of the delivery tube.

FIG. 10a shows a holding balloon with embedded tubular cutting device and explorer guidewire.

FIG. 10b shows the inflated tubular push-blade with blade exposed.

FIG. 12c shows the plane and tangential angle at another point on the stem.

FIG. 12d shows the plane and tangential angle with cross-sections of two different grafts of different thicknesses which illustrates the longer distance the stiff suture must travel for greater thicknesses of graft and also how the stiff suture must be pointed back toward the target point on the brim for obtuse angles.

DETAILED DESCRIPTION OF THE PREFERRED EMBODIMENTS

Figure 1:
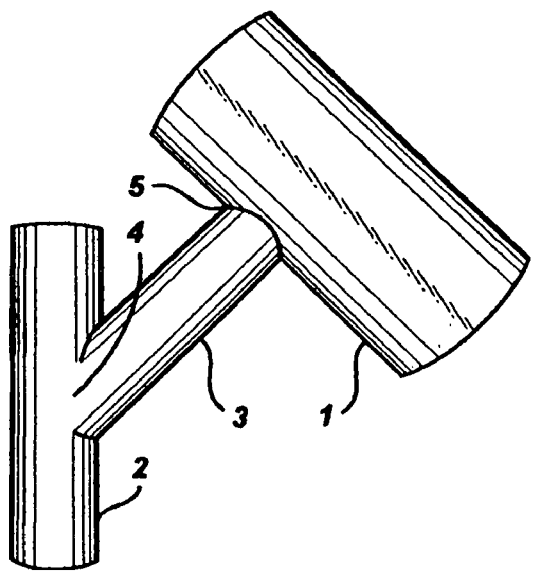
FIG. 1 shows two tubes joined by a graft, visually the same product of the present invention and prior art.

FIG. 1 shows the product of the present invention that is visually the same as that of prior art; the sides of a mammalian first tube 1 and second tube 2 connected by the transected ends of a graft 3. The transected ends of said graft are also identified 4, 5. The present invention has additional features that are not part of prior art, including a doubly sealed graft, no more collateral damage to the body than percutaneous entry, suturing accomplished in as many seconds as manual suturing requires minutes, no need to stop the heart more than for a few seconds in coronary bypass applications and potential for a larger population who can tolerate a procedure that may be virtually out-patient.

The innermost endothelial linings of two tubes, called intima, should be in contact all along their circumference for a graft to grow properly. The prior art leaves this to the surgeon's eye-hand coordination skill and a scissors. Many patent applications ignore the need or even thwart it in some ways. But in the preferred embodiment of this patent application means of accomplishing this intimal contact are provided without the surgeon's manual suturing skills, the imprecision of a scissors snip, the maceration of tissue, inadvertent or intentional separation of intimal layers. This process starts with graft 3 being prepared prior to the operation.

Figure 2A:
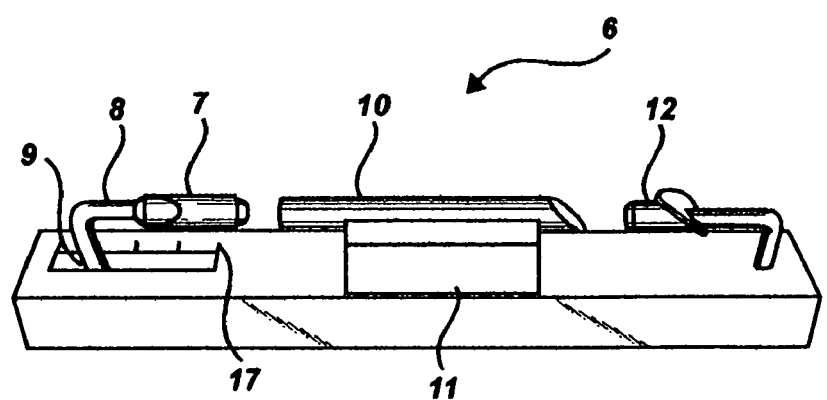
FIG. 2a shows the preparation bench on which the graft is prepared prior to the operation.

FIG. 2a shows a device called a preparation bench 6 for preparing graft 3 prior to the operation. Cutting sleeve 7 is mounted on support bracket 8. The support bracket is movable along a measured slot 9 with measurement marks 17. This provides the means for accurately cutting the graft to the correct length. One cutting sleeve provides the means of making the transected end 5 of graft 3 the correct circumference and shape. The other cutting sleeve is for the other end 4 of said graft 3 and the second tube 2. The two shapes are based on the shape of the junction between said graft and first tube and said graft and second tube (usually different). The junction of the end of one cylinder (e.g., graft 3) and the side of another cylinder (e.g., either tube 1 or 2) is a complex three dimensional oval curve that is a function of their relative sizes and the angle at which they are joined. Along the center of the bench is the delivery tube 10 on a rest 11. A graft core 12 is shown mounted on the other support bracket. Graft core 12 is placed there after both graft ends are cut and shaped. Then one sleeve is removed and replaced by graft core 12. The cutting sleeve and graft cores are the same dimensions and so fit on the same supports. The end of the graft is taken from the cutting sleeve and placed on the graft core and sutured there.

The graft 3 with graft cores 12 sutured to each end, will be encapsulated inside the delivery tube 10 as the final step accomplished on the bench 6. The graft cores 12 will be slightly compressed as they are pushed into the ends of the delivery tube 10. So the graft 3 must be placed in the delivery tube while its ends are free of these graft cores 12. The details of the graft cores will be shown and discussed after the preparation process with the cutting sleeve 7 is finished.

The length of the bench 6 as shown is somewhat shorter than the typical size in an application in order that both ends can be seen clearly in one figure. The bench must be securely fastened to a stable table for use.

Figure 2B:
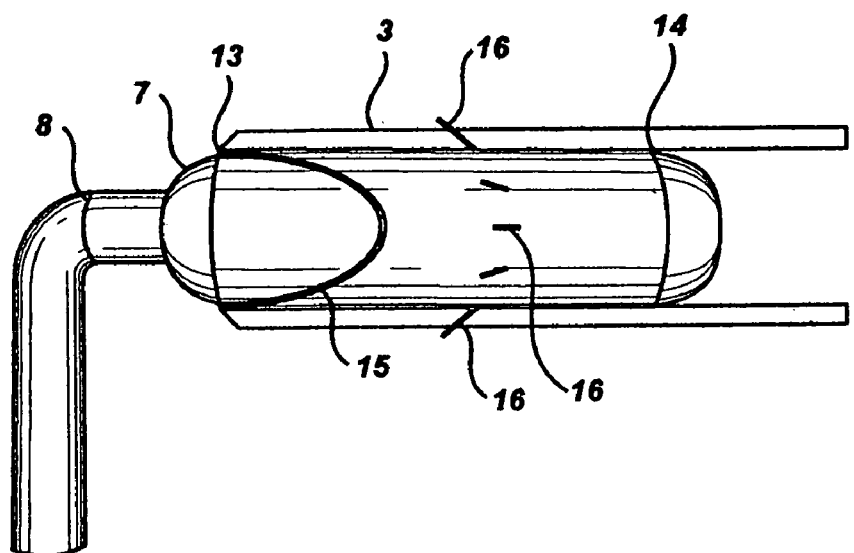
FIG. 2b shows a cross-section of graft mounted on a cutting sleeve used to prepare the graft.

FIG. 2b shows a detailed view of a cutting sleeve 7 of the correct diameter mounted on the support bracket 8. The basis for selecting the correct outside diameter for the sleeve 7 is the estimated diameter of the smaller of the two tubes 1, 2 less (about) twice the thickness of the wall of the graft. One end of graft 3 is drawn up to mark 13. Graft 3 is shown only in cross-section as a white space at the top and bottom of the sleeve so the elements of the sleeve can be viewed. To make the ends of said graft the same diameter as the cutting sleeve, a cut is made with a scalpel on the longitudinal axis of the graft from mark 13 to the sleeve's base 14. This cut is where the white cross-section of the graft is shown on top of the sleeve. Folding the cut sides of the graft together, another (almost parallel) cut is made such that the two sides come together evenly. This is done so the end of the graft will fit snugly (without pulling) around the cutting sleeve 7. If the part harvested as a graft is a vein, the direction of flow in its lumen must be in the same direction as in its previous location. Thus veins are reversed bringing their smaller diameter to join the (larger) first tube and larger diameter to the second (smaller) tube. Slitting the graft during preparation allows the circumference of the two graft cores to be the same—the same size as the stems which are the same diameter. The size of the opening in the first tube must be the same size as the opening made in the second tube and that circumference must be the same as that of the stem(s). Problems regarding fluid flow are thereby minimized.

The guiding groove 15 is a template for inserting a scalpel and guiding it along the groove. Said groove 15 is in the shape made by the end-to-side intersection of two cylinders at the angle the user intends to use in the application. The internal angle of said groove is continuously varying along its sinuous path. It guides the scalpel to cut an acute bevel on the graft. This bevel is cut back from the innermost layer of the graft to the outermost layer in order to expose the inner layer without outer layers overlaying it. This acute angle varies for every point on the junction and is one-half the tangential angle between graft and tube at that point. This tangential angle may be determined by erecting a plane at a right angle to the tangent at a given point on the junction. This plane will intersect graft and tube to display the angle between them. The miter angle between graft and tube is one half the tangential angle. It provides half the space for the graft end and half for the wall of the open tube. In this way the intimal layers of graft and tube are exposed to each other around the circumference of the anastomoses. This is best described in the context of graft cores 12. It is sufficient to point out here that the shape and angles imposed by this guide are more complex than can readily be made free-hand with scalpel or scissors.

Short hypodermic needles 16 are pushed by a lever through holes and on through the graft 3. A vacuum may be introduced through the needles in situations where greater precision is desired. With or without vacuum, the preparer anticipates and coordinates this action with use of a sponge for pressing graft 3 gently against the needles 16 as they emerge and pass through the graft 3. The needles deposit a small amount of marker dye so the locations on the graft 3 will be apparent when it is mounted on the graft core 12. The number of hollow needles 16 varies with the application, but for convenience the number twelve will be used here with the understanding that the term "or whatever number" will not be used over and over in this description each time it is appropriate, but is intended as generally applied. The spacing of the needles can also be varied. For instance there may be two close together and then a larger space to the next one, etc. Again, only for convenience of discussion these twelve will be placed at the twelve "clock" positions.

At the other end of the bench the other end of tube 3 is on a cutting sleeve 7 that has a groove based on the junction between that end of the graft and the tube to which it will be joined. At this step the graft is measured for the exact length desired. The supporting bracket 8 for said cutting sleeve 7 is mounted in a slot 9 where it can be moved back and forth and locked in place at the measurement mark 17 that reads the distance between the guiding grooves 15 on the two sleeves. This end of the graft is drawn so it is without kinks but not tight and placed on the other cutting sleeve, as the preparer sets the desired length on measurement mark 17 of slot 9. It is the distance between the sites chosen for anastomosis on the first and second tubes and must not be too long or the graft will form kinks that inhibit flow, or so short that the graft 3 will not reach or be somewhat stretched between the selected sites. The desired sites and length are determined by ultrasound or other devices prior to preparation. The scale on the slot 9 provides that the desired length is the length actually cut. When the cutting process is completed on the second sleeve, one cutting sleeve 7 is removed from its mounting bracket and a graft core 12 put on that support bracket 8. Since all devices are sized to work together the graft core has the same inside diameter as the cutting sleeve and fits on the support bracket in the same position.

Figure 3A:
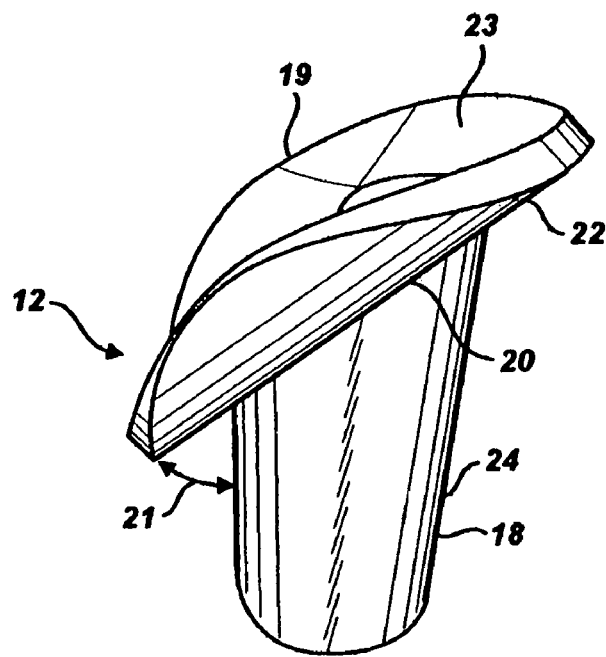
FIG. 3a shows a graft core with stem and brim.

FIG. 3a shows graft core 12. The core consists of a stem 18 and a brim 19. The junction 20 between the two is a complex curve created by the intersection of two cylinders and matches the size and shape of the guiding groove 15 on the cutting sleeve 7. The angle 21 at which the longitudinal axis of the stem 18 intersects the longitudinal axis of the brim 19 may be at any angle. In certain application situations, e.g., CABG, surgeons prefer angles between thirty and forty-five degrees (plus or minus). Each possible angle of intersection 21 produces a different complex curve for the junction 20 and a different set of tangential angles between the stem and brim at each point around the junction. However, it is cumbersome to show figures with several angles 21 and a set of tangential angles for each. So this patent application will use forty-five degrees and mean any number, plus or minus from that. And the tangential angles at the representative clock positions will be used as illustrative of all such angles. In some few cases ninety degrees will be used for illustrative purposes. Each application situation has tubes of characteristic dimensions, but the relationship of the dimensions of the suite of devices in the preferred embodiment of this invention remain (approximately) the same.

The outside surface 22 of the brim 19 has the curvature and dimensions of the lumen of the tube into which it is to be placed in intimate contact and thus create a seal. The lumens of body tubes have deviations from being perfect cylinders for various reasons. And the brim may deviate from a perfectly smooth surface if it is found advantageous to place a small trench and bump to catch stiff sutures that enter the brim at a very oblique angle. Whether this 'imperfection' in the surface would promote a blood clot is not known but probably not as the stiff suture in the trench might create sufficient surface tension to keep fluid from entering the trench. So, while perfection is not possible, certain rules-of-thumb are followed to make the fit as good as practicable. For instance, in the case of a lumen of 3.5 millimeters (its diameter) the curve of the outside surface 22 of brim 19 has a radius of 1.75 millimeters. The rule-of thumb for the thickness of the brim is about ten percent of the diameter of the lumen of the smaller of tubes 1 and 2. Thus the brim which is to be placed in the smaller lumen of 3.5 mm would have a thickness of about 0.35 mm. That thickness makes the radius of curvature of the inside surface 23 of the brim (about) 1.05 mm. That is 1.75 mm minus two times the 0.35 mm. thickness, i.e., 1.75− 0.7=1.05. The stem 13 has an outside surface 24 radius about equal to the inside surface 23 radius of the brim 19 and a thickness about the same as that of the brim (0.35 mm in this example). In addition the brim is flexible and thus adjusts its shape to that of the lumen for a seal that is at least temporarily a good one. When sutures enter the brim and draw it into tighter contact with the lumen the resulting flexible seal is better than can be achieved by pressure from the fluid alone (as with other patent applications) and the sutures add the second seal that is the only seal under prior art.

The outside surface 22 radius of the brim 19 of graft core 12, to be placed in the larger lumen of the first tube will have the curvature of the radius of that lumen. But the stem 18 of that graft core 12 will be the same size as the stem 18 of graft core 12 for the (usually smaller) second tube. The thickness of the stem 18 and the brim 19 is the same or similar for the distal and proximal graft cores. If the lumen of the first tube 1 is several times the diameter of the second tube 2, the radius of curvature of that brim is fairly flat with respect to the curvature of the brim that is lodged in the smaller lumen. This would be the case in a situation where the second tube is a corollary artery and the first tube the ascending aorta. The exact sizes of the two tubes to be joined will vary by application situation but the size relationships noted here should be considered as useful rules-of-thumb for sizing a package or kit of coordinately sized devices for a given application situation.

Figure 3B:
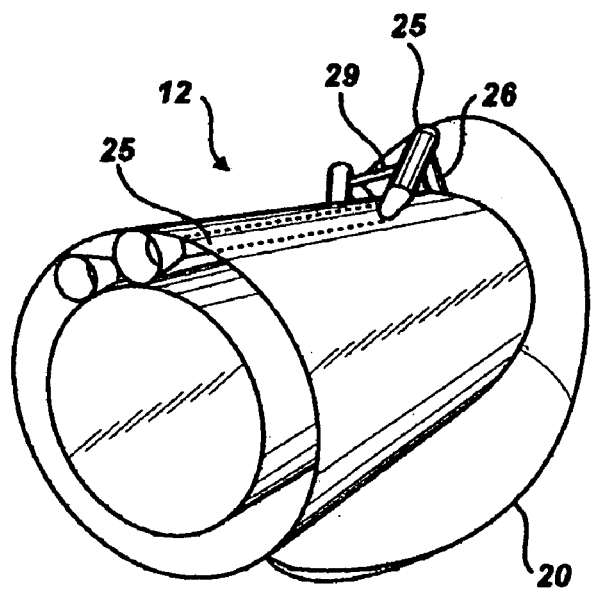
FIG. 3b shows a view of the graft core with two hollow sutures inside the stem and posts snapped on their ends with a segment of circular suture between said posts.

FIG. 3*b* shows another view of the graft core 12. In this view the base of said graft core is shown as open so two of the (nominally) twelve hollow sutures 25 inside the stem can be seen. In this figure the hollow sutures 25 start at the base of the graft core and make a forty-five degree turn to come out of the stem radially at a certain angle and distance from the junction 20 of brim and stem. This distance is a function of both the tangential angle between the stem and brim and the thickness of the graft. The angle at which the hollow suture exits the stem can be any acute angle, but 45 degrees and 30 degrees are used as examples. The thickness of the graft affects how far the lip of the brim should be extruded beyond the stem as well as the length of the stem. These relationships are described in a later paragraph along with illustrative tangential angles between brim and stem.

These tangential angles are determiners of how far each stiff suture must be driven to enter the brim, along with the thickness of the graft. The perpendicular distance between the surface of the stem and the end of the hollow suture 25 is slightly more than the thickness of the graft so the hollow suture end will extend slightly beyond the graft. The two hollow sutures shown here represent the (nominally) twelve that are located at the clock positions. The 6 o'clock position is in the "heel" and the 12 o'clock position the "toe" position, using the "foot' terms common in the context of CABG procedures. Each hollow suture 25 will be placed in one of the dye-marked holes cut in the graft by hypodermic needles 16.

The ends of the hollow sutures that come out of the surface of graft 3 are all at the same distance from the junction 20. There is a post 26 for each hollow suture. The length of the post depends on the thickness of the graft and the acuteness of the tangential angle between brim and stem at the point on the junction where the post is placed to meet its corresponding hollow suture. The opening at the end of each hollow suture 27 is oriented toward the brim. The exact orientation is a function of the angle between brim and stem.

Figure 3C:
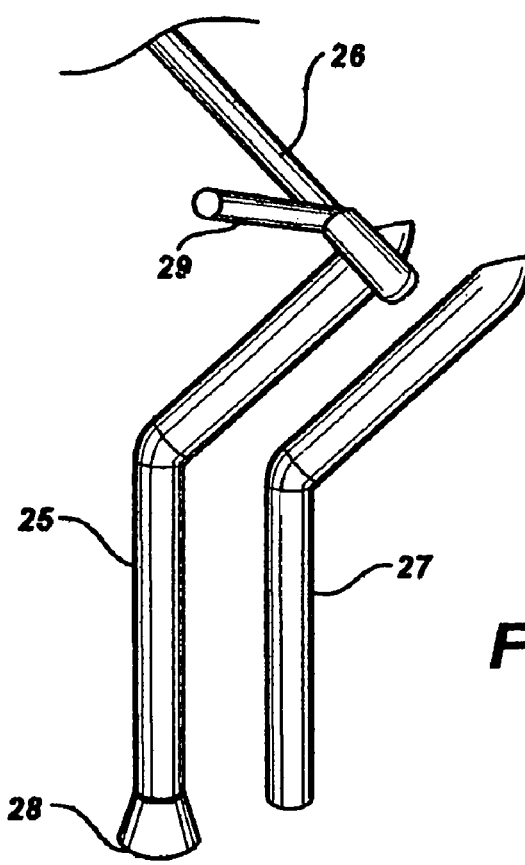
FIG. 3c shows the relationship of hollow and stiff sutures with posts and a segment of the circular suture.

FIG. 3*c* shows the size relationship of the stiff suture 27 to the hollow suture 25. The post 26, when pressed and snapped on the end of the hollow suture 25 (as shown) holds it in place and is the second side of the suture holding the graft to the stem 18. One segment of the circular suture 29 is shown attached to the post. A hollow cone 28 flares from the base of each hollow suture 25. The stiff suture is shown outside the hollow suture here, but in practice it is located inside the hollow suture. One segment of circular suture 29 which connects all posts in a ring is shown. When a metal rod (not shown in this figure) of the same diameter as the stiff suture 27 is introduced into the hollow cone 28 at the base of the graft core it rests against the stiff suture 27. Pushing the rod while holding the graft core 12 drives the stiff suture out the end of the hollow suture through the wall of tube 1 or 2 and into the brim 19. The stiff suture 27 is barbed so it will not retract once driven forward. The barbs are lodged in the brim 19 and in the hollow suture 25. The length of the driving rods is such that they drive the stiff sutures the correct distance for entering the brim. These operations are introduced at this point to aid in describing the graft core 12. There is work with the graft core on the preparation bench 6 before the stiff sutures 27 are driven during the operation.

Figure 3D:
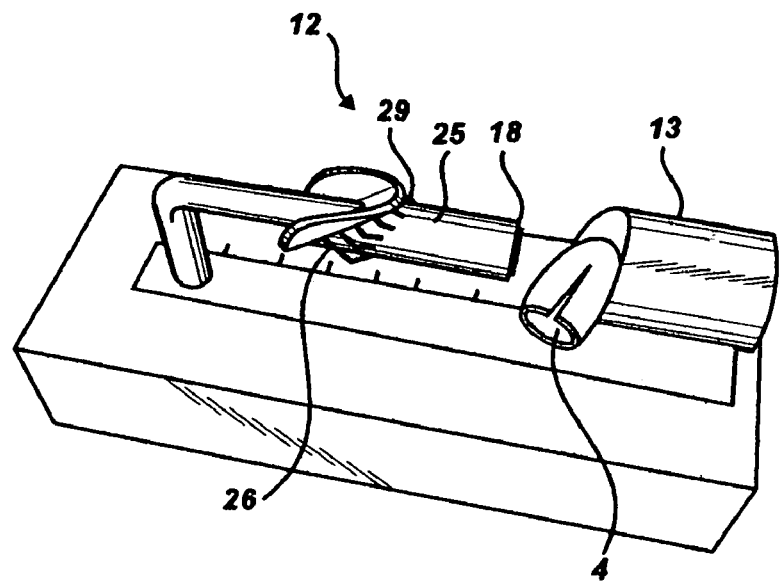
FIG. 3d shows a graft core with posts, hollow sutures and circular suture ring on the preparation bench with the graft coming out of the delivery tube ready to be mounted on the stem.

FIG. 3*d* shows one end of the preparation bench 6 with a graft core 12 mounted in place of the cutting sleeve. The preparer normally places the end of the graft directly on the graft core after said sleeve is removed from the support arm 8. For purposes of illustrating what the end 4 looks like it has been allowed to hang out of the delivery tube 13 with the slit showing. The preparer utilizes the flexibility in circumference provided by the slit to wrap the end 4 around the stem 18 of the graft core 12 where the (nominally) twelve hollow sutures 25 are sticking out. The slit enables the preparer to slip one hollow suture 25 at a time through the dye-marked openings in the graft 3 as its end 4 is wrapped around the stem 18. The hollow sutures 25 are shown emerging from the stem 18 and the posts 26 coming from the junction with rings on their ends for snapping on the hollow sutures and the circular suture 29 tying together the ends of the posts. At the time of manufacture the posts are connected in the circular suture 29 except for one or more open link(s). The open link(s) allows the circular suture to be pushed away from interfering with the manipulation of hollow sutures and posts.

Figure 4A:
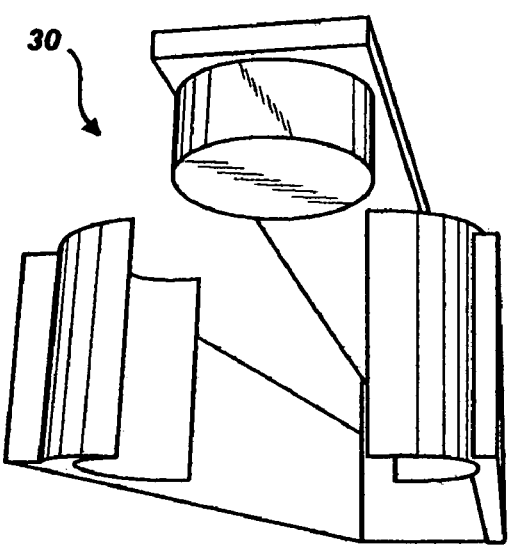
FIG. 4a shows the device for snapping together posts and hollow sutures.

After the ring on each post has been snapped on its hollow suture by a snapper device shown in FIG. 4*a*, the open link of the circular suture is snapped together. This makes the circular suture the circumference and the posts spokes going back to the junction 20. The purpose of the circular suture is to stabilize the location of each hollow suture and to prevent the individual hollow sutures from being forced backward when the stiff sutures are driven forward from their ends. As the stiff sutures all push through the wall of the tube being anastomized to the graft, there is considerable back pressure on the ends of the hollow sutures from which the stiff sutures issue. This circular suture 29 will not increase in circumference and so tends to prevent the hollow sutures from backing up. The hollow sutures and posts are manufactured so the exit point of each hollow suture is pointed at the outer circumference of the brim. At certain clock positions this is straight out, at others there is an inward bend. This makes the stiff sutures inside the hollow sutures pointed at their target on the brim.

Figure 4B:
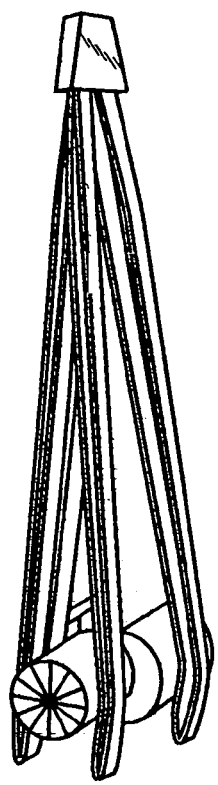
FIG. 4b shows the compression tweeze device for compressing the brim of the graft core and pushing it into the delivery tube.
Figure 4C:
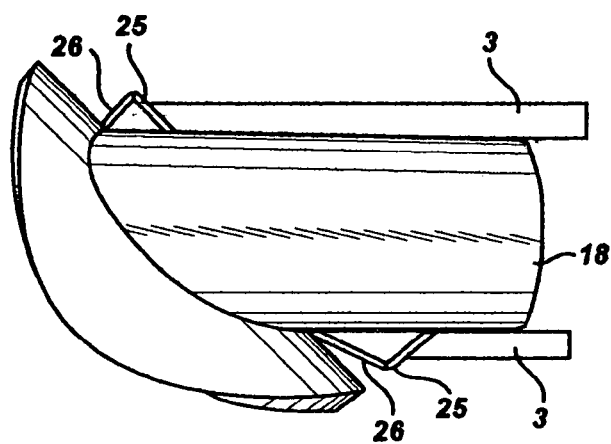
FIG. 4c shows the cross-section of a prepared graft sutured on the stem of a graft core at the 6 and 12 o'clock positions by hollow sutures and posts. Angle of intersection and tangential angles are equal in this position.
Figure 4D:
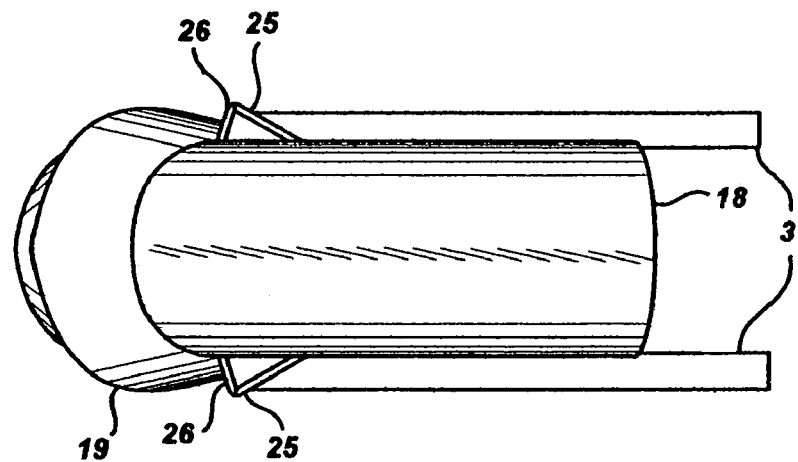
FIG. 4d shows the same elements as shown in FIG. 4c at the 3 and 9 o'clock positions, noting how hollow sutures must point stiff sutures back toward the stem's longitudinal axis to intersect the brim from this position.
Figure 4E:
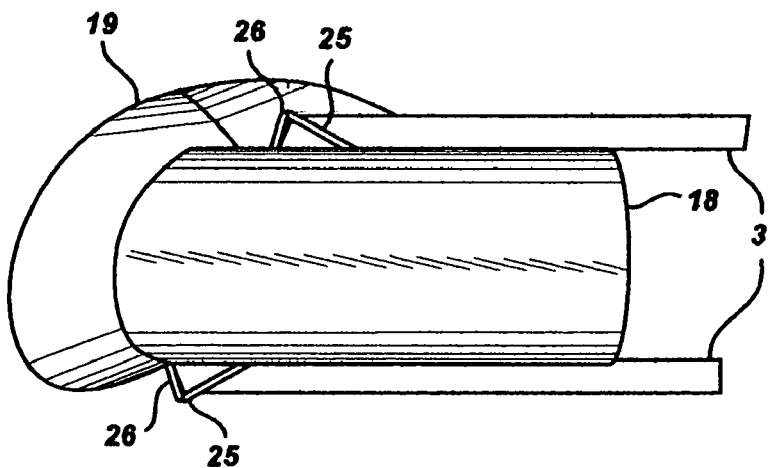
FIG. 4e shows the same elements as FIG. 4c but at the 4 and 10 o'clock positions.

FIG. 4c shows a cross-section of graft 3 mounted on the stem 18 by hollow sutures 25 and posts 26. The angle of intersection of the longitudinal axes of stem 18 and brim 19 is 45 degrees as seen in the angle at the bottom of the figure (the 6 o'clock position). The complement of 45 degrees is 135 degrees, as seen between the stem and brim at the top of the figure (the 12 o'clock position). At the 6 and 12 o'clock positions the tangential angles are the same as the angles of intersection. One half of the tangential angles is the miter angle. The end of the graft is cut to this angle by the guide on the cutting sleeve and is shown cut to that miter angle in the figure. The miter angle is also the angle of the post, as likewise seen in the figure. The miter angle leaves an equal amount of space for the wall of the tube as it folds around the brim and therefore an (approximately) equal amount of wall tissue for the stiff suture to cut through on the way to the brim. The hollow suture is shown emerging from the stem at an angle of 45 degrees. This angle could be some other value but 45 degrees allows a proper "bite" of graft tissue to be caught in the triangle between hollow suture, post and stem. The graft is thus sutured to the stem during the preoperation preparation. All that remains to complete the suturing is pushing the stiff sutures inside the hollow sutures through the wall of the tube and into the brim. FIG. 4d shows a cross-section of the graft on the stem at the 3 and 9 o'clock positions. At these positions the angle of intersection and tangential angles are different. The tangential angle between stem and brim is about 167 degrees at these positions. The miter angle is half the tangential or about 84 degrees and the graft is shown as cut to that angle by the guide on the cutting sleeve. The post emerges from the junction at that angle and the hollow suture shown emerging at 45 degrees. The angle at which the stiff suture must emerge from the hollow suture is also about 84 degrees back toward the longitudinal axis of the stem. This is in order to intersect the brim. FIG. 4e shows the 4 and 10 o'clock positions for the same elements. In this case the hollow sutures point the stiff sutures approximately in line with the longitudinal axis of the stem.

The process is repeated on the other end 5 of graft 3. The slits in the ends 4, 5 of the graft 3 are now sutured together by hand. When this is accomplished graft 3 is sutured to a graft core 12 on each end. After the graft cores are sutured to each end of the graft the preparation on the bench is finished by using a compression tool 30 shown in FIG. 4b to compress the brim and push it inside the delivery tube (still on its rest on the bench). When this is accomplished on both ends, the delivery tube is connected to a delivery catheter of the same diameter and of an appropriate length for conducting the operation.

The graft core is fabricated from biodegradable or biocompatible material. Biodegradable if the stoma is to be physiologic. Biocompatible if the graft core and graft are to remain in the body permanently. Suitable biodegradable substances are certain collagens, sugars, hydrogels, lactides and other material known to have a certain period for absorption by the body (resorbtion). Biocompatible materials include certain polymers, elastomers and silicones. The sutures of the graft core may be of the same or similar material, but of different characteristics. The hollow sutures are bonded inside the body of the stem ending at the base of the stem and may be made of a slightly harder material than the stem to facilitate the smooth forward movement of the stiff sutures inside them, but not so hard that the barbs on the stiff sutures will not engage. The stiff sutures are made of a still harder and stiffer form of the same biodegradable material as they must puncture the brim as well as the walls of the first and second tubes. The material for stiff sutures must bend sufficiently as to bulge slightly if the tube in which the graft core is lodged moves with the beat of the heart. The entire core, brim and stem will move with the beat but the brim may be affected first and thus the need for a slight bending of the stiff suture until the stem follows. The ends of stiff suture must retain a sharp edge to reduce friction as they are driven through the walls and brim. Since the brim is compressed when placed in the delivery tube, the brim must be manufactured of pliable material that will return to its original shape after this deformation. The brim is also soft enough to allow puncture by the stiff sutures. Chemicals for stimulating growth of the grafts are imbedded in the junction between brim and stem at manufacture. Chemicals to make the openings in walls slip over the brim in the desired direction may also be applied.

Applications where the graft core and graft are to remain in the body permanently are bonded together. They may be made of the same or different material at the factory. In any case, the hollow sutures are made of a harder inert material than the graft core, and the stiff sutures of an even stiffer material. An epoxy glue of the type that bonds when the A and B parts are mixed may be used to make a long-lasting bond between stiff sutures and the brim. Part A is in the brim and part B on the stiff sutures. The thin layers of A and B mix as the stiff sutures move through the brim. The stiff sutures must be of a material flexible enough to resist breaking from a plurality of heart beats if they are flexed for years of such beating.

Figure 4F:
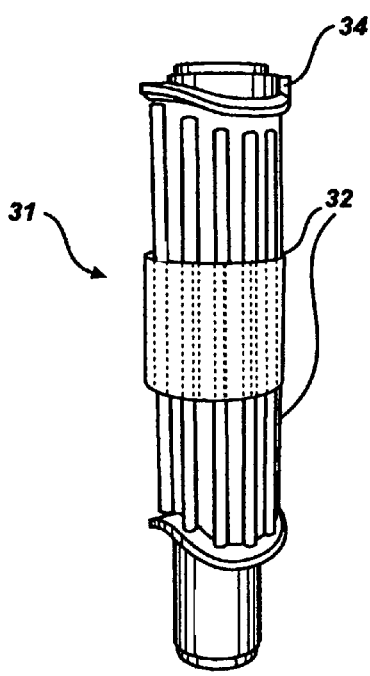
FIG. 4f shows a rodding balloon with rods pointed distally and proximally.

FIG. 4f shows a rodding balloon 31. Its twelve rods 32 are exposed in the distal and proximal directions so that it can be used for pushing the stiff sutures 27 in the distal graft core 12 through the second body and then without having to remove the rodding balloon, its proximal rods are used to pull against the stiff sutures 27 in the proximal graft core 12 driving them through the first body part. The rodding catheter 33 to which the rodding balloon is attached is also shown. The key 34 is also shown as it is attached to the distal end of the catheter. This key is small but can be seen in this view. The function of the key will be discussed in the context of the figure which shows the matching keyway inside the stem of the graft core—where it is almost hidden from view. When the rodding balloon 31 is advanced, the rods 32 push the stiff sutures 27 from the base of the core stem to the point where it turns at forty-five degrees (for instance) to emerge from the stem. This action moves the stiff sutures 27 into the brim. The stiff sutures have barbs on their surface to keep them in the position to which they are advanced. These are embedded in the brim and in the hollow sutures from the point where they turn to emerge from the stem. If the bond of stiff suture and brim is not strong enough a small amount of appropriate glue may be added at the place where the stiff suture enters the brim. This action with the rodding balloon is performed later, when the brim is inside the lumen of the second tube. The purpose in introducing the rodding balloon now is to show how the stiff sutures are driven. More details regarding the rodding balloon and the graft core 12 will be shown when the brim is in the lumen of the second tube 2 and the stem in the artificial opening slit in the wall of the second tube. A less preferred embodiment of the rodding balloon is to utilize two, a distal and a proximal, with rods facing in only one direction. This alternative embodiment is sufficiently obvious as not to need an illustration. The advantage of combining rods in both directions is that one rodding balloon need not be withdrawn for the other to be advanced. If there are application situations where the anastomosis with the first tube 1 is much larger than with the second 2, one rodding balloon 31 may not be capable of changing diameter to the extent necessary. Then distal and proximal rodding balloons of different sizes would be required.

Cutting devices are needed to exit the first tube and enter the second tube. There are a variety of conditions in which the tubes of the body exist. It may be expected that cutting devices of various types will be needed for this diversity of conditions. To accommodate this, five alternative embodiments of the invention provide five cutting devices. Each is designed for use in certain conditions that would be encountered in an application situation. Variations on these five are obvious.

Figure 5A:
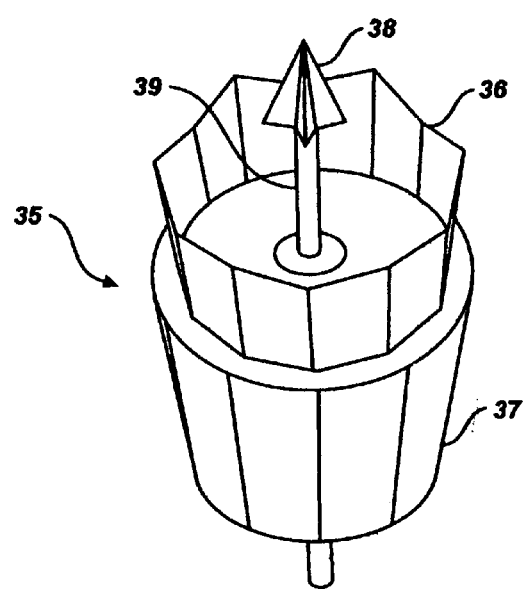
FIG. 5a shows circular excision device with conical dart.

FIG. 5a shows the embodiment of circular excision device 35 in the inflated state. A relatively large diameter first tube is required to maneuver this device to a position of about ninety degrees with respect to the tube wall. The circular microtome blade 36 excises a disk of tissue. The advantage of a disk is that the endothelial layer is thus equally exposed around the entire circumference. This is not the case with a slit. It is not the case with devices that twist their way through said wall throwing off bits of tissue like a meat grinder. The cruciform conical arrow 38 and its guidewire 39 are manipulated independently of the balloon and pass through a tunnel in the center of the balloon. The balloon is mounted on a catheter advanced through the clamping catheter to the target site of anastomosis. The clamping catheter is maneuvered to about ninety degrees with respect to the wall at the target site. The balloon is inflated causing the circular microtome blade 36 to extend from the distal end of the balloon as shown. The cruciform conical arrow 38 is pushed by its guidewire 39 out of the tunnel running through the balloon and through the wall of tube 1. The serrated microtome blade 36 is pushed forward cutting a disc of tissue from the wall. Blade 36 has sufficient depth to cut entirely through (the expected) thickness of the first tube wall so there are no tissue connections holding the disc to the wall. The blade is serrated to engage cutting the tissue at an angle. The number of serrations is variable. The four shown are merely for example. The shape of the serrations is such that no twisting of the blade is needed. That is because in many applications, including those in the aorta, twisting the catheter on which the balloon is mounted would be likely to move said catheter away from its location. Radiopaque markers on the blade serrations show on the fluoroscopic equipment when the blade is through the wall. At this point the conical arrow 38 is withdrawn into the balloon tunnel. The balloon is deflated. This returns the blade to a protected position inside the excision balloon 37. The balloon 37 and conical arrow are withdrawn into the tunnel in the balloon with the tissue disc spitted on the guidewire 39. The blunt proximal side of the conical arrow 38 keeps it on while it is safely put away in the tunnel. Said device is removed through the clamping catheter outside the body.

Figure 5B:
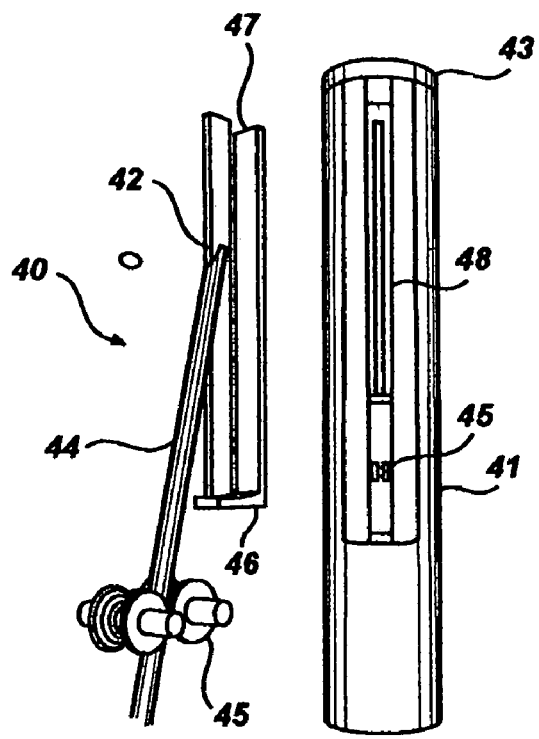
FIG. 5b shows a cylindrical cutting arm device.
Figure 5C:
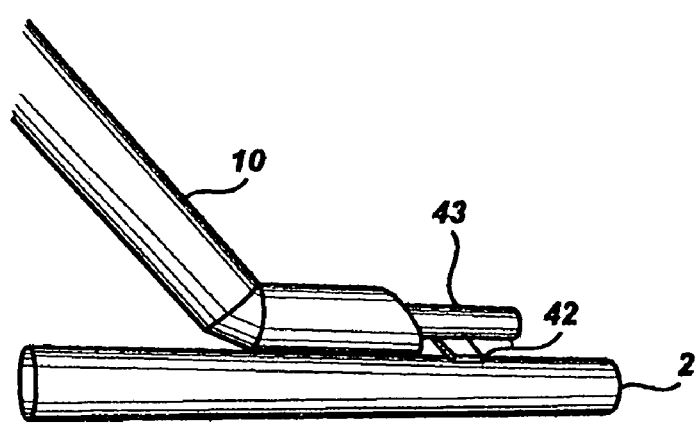
FIG. 5c shows a cylindrical cutting arm device mounted in a catheter.

FIG. 5b shows the cylindrical slicing device 40 in two views, inside and outside the cylinder 41 that encases the mechanism. This device is used in situations where the blade arm 42 must operate at (more or less) right angles to the axis of the catheter in which it is advanced. Cutting device 40 requires a situation where there are no body parts in the arc of the blade between the catheter and the tube being cut. The cylinder 41 encasing the microtome blade arm 42 is of a diameter to fit snugly in the catheter through which it is advanced. A radioplaque marker 43 on the distal end of the cylinder is compared to a marker on the end of the delivery tube 10 to advance the cylinder sufficiently to expose the slot 48 in the cylinder through which the blade arm 42 will travel, while leaving a sufficient portion of the cylinder 41 inside the clamping catheter for support. The operator pulls back on the control (not shown and exterior to the mammalian body) which draws the guidewire 44 back between two pulleys 45 embedded in the wall of the cylinder. This deploys the blade arm 42 through its arc. The blade arm is attached at the proximal end to a spring 46 whose other end is connected to a support rod 47. The support rod 47 is embedded in the cylinder wall opposite the slot 48 where the blade arm emerges when pulled. Once the cut is made the spring returns the blade arm 42 inside the cylinder 41. FIG. 5c shows this device 43 being advanced forward of the delivery tube 10 to cut a tube 2 with blade arm 42.

Figure 5D:
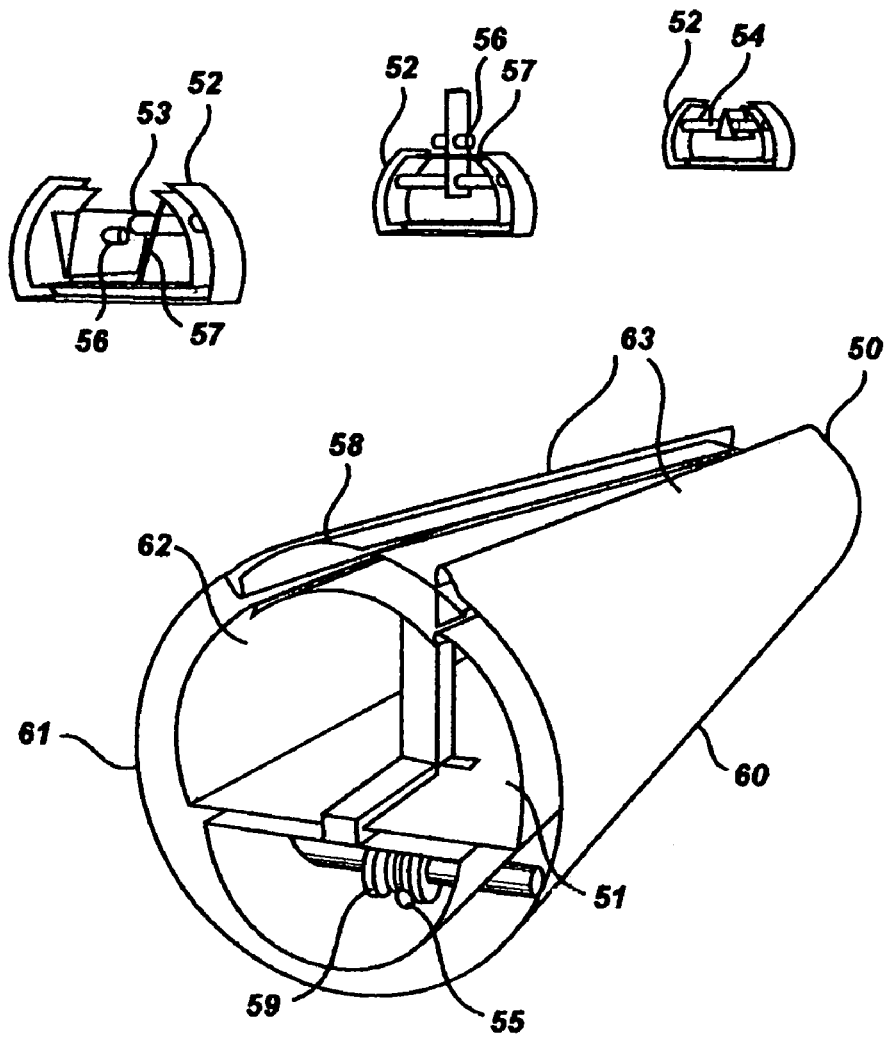
FIG. 5d shows a tracked slitting device with three views of blade mounted on cart as it is at successive positions along the track.

FIG. 5d shows two views of a tracked slitter 49. This form of cutting device has the advantage of not needing to be deflated after cutting. Said device may be advanced into the lumen immediately as the blade is hidden at the end of the track. It's track 50 is shown here as a cylinder with a slot above, except at its end. The track 50 could be of a different shape. The important characteristic of said track is that it is slidably engaged with a moving element 52 so as not to wobble or twist as it is drawn through the tunnel 51. The moving element 52 is shown at three locations along the track, beginning, middle and end. Said moving element 52 is shown above the track so as not to obscure it from view. The moving element 52 has a slot in it to accommodate the swivel blade 53 when it rises. The swivel blade is pivotally mounted on axle 54 that turns in the body of the moving element 52. The swivel blade's original position in the track is lying flat in the tunnel, blade up. When the blade is pulled by a guidewire 55 (not shown in its entirety as its path is obvious as it extends above the slot in the track and it would obscure many things if shown) attached to a pin 56 extending from the side of the blade, the swivel blade rises to the erect position (center image). The blade is held there by a bar 57 across the moving element. Continued pull on the guidewire 55 drags the erect blade 53 along the length of the track. The track can be any length. The blade may be any length. The blade cuts as it moves. When it is a little more than blade's length from the end of the track, a lever 58 attached to the top of the track engages the bar 57 and pushes it down. Bar 57 drops, and without it to hold the blade erect, the blade 53 drops as well. The blade descends into the track tunnel, blade down. The pulling guidewire 55 leads to a pulley 59. The pulling guidewire turns back 180 degrees on said pulley 59. Said guidewire leads to another pulley 60 near the midpoint of the track (not visible in figure) where it turns ninety degrees on that pulley and exits at the midpoint of the track. Said guidewire then continues in the delivery tube and back to the operator. Continued pulling on this guidewire pulls the moving element through a hinged bar 61 into a receptacle 62 where the cylinder 50 is covered. The hinged bar is spring-loaded and closes behind the moving element. Pushing back on the pulling guidewire 55 does not open the door or free the moving element from the receptacle. A push on the guidewire 55 releases the latch that holds the two halves of the track together. This causes the track to unlock from its straight position and bend at the middle. The hinge 63 on its upper side swings so the two halves of the track fold against each other. Now pulling on the pulling guidewire 55 draws the folded track back through the delivery catheter. The folded track occupies only a small space and so can be withdrawn through a small opening. The tracked slitter may be removed with the holding balloon on which it is mounted or drawn through the center opening in the holding balloon.

Figure 5E:
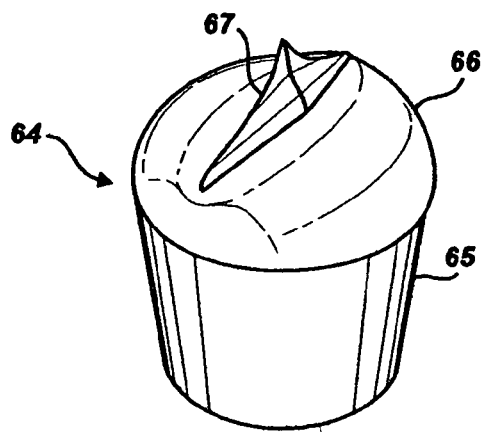
FIG. 5e shows a circular push-blade cutting device.

FIG. 5e shows a circular push-blade balloon 64. It is an alternative to the circular excision device. It does not require a ninety degree (square) approach to the wall to be cut. However it cannot be used at an angle much more acute than that.

It has the advantage of moving forward with the catheter behind it also moving forward. It may be used with the first or second tube, so long as the second tube is large enough that the blade does not endanger the side opposite the cut. Either way it may save some seconds in moving the catheter forward after cutting. This may be of primary importance in some situations. It consists of a non-compliant body 65, a compliant extender 66 which exposes the microtome blade 67 when inflated. When the balloon is semi-deflated the blade folds into the extender 66 and the extender folds back into the body 65 of the balloon.

Figure 5G:
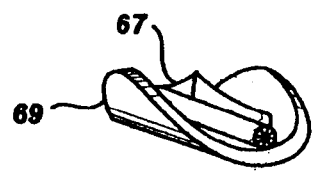
FIG. 5g shows an inflated tubular cutting device with blade exposed and mounted on a holding balloon.
Figure 5H:
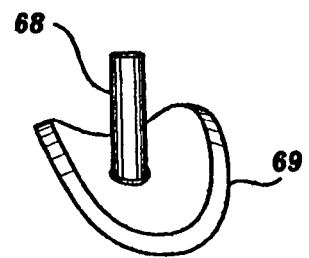
FIG. 5h shows a tubular push-blade device deflated, folded and ready for withdrawal.
Figure 5F:
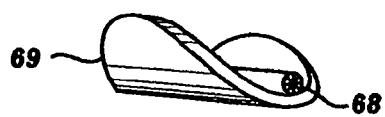
FIG. 5f shows a deflated tubular push-blade cutting device mounted on a holding balloon.

FIG. 5f shows the deflated tubular push-blade balloon 68 as it is normally mounted, on a holding balloon 69. FIG. 5g shows the tubular push-blade balloon 68 inflated to extend the blade. The tubular push-blade balloon 68 has the advantage of saving seconds in certain situations. Its disadvantage is when the second tube is small, the blade may be pushed forward too far and cut into the other side. If used with a small second tube the push-blade balloon must be deflated immediately after cutting to protect the opposite wall of the second tube from injury caused by an exposed blade. The holding balloon 69 is of the same shape as the brim which it holds and the same radius as the inside surface of the brim being held. The holding balloon has its own inflation lumen and guidewire (not shown). FIG. 5h shows the tubular push-blade deflated and folded ready to be withdrawn through the center opening in the holding balloon. In some situations the tubular push-blade balloon will not be folded and withdrawn before the holding balloon is also folded and withdrawn.

Equipment common to PCI catheter labs are fluoroscopic devices for viewing tissue, radiopaque markers and contrast emitted from catheters. The screens on fluoroscopes often show the target from different directions allowing the Interventionist to combine images in a mental three-dimensional view. These devices help thread a guiding catheter through the branches of the femoral artery into the ascending aorta, and then position the catheter at a right angle with respect to the ostium or entry point to the targeted coronary artery. These devices and other localizing equipment are appropriate for use in the present state-of-the-art applications, examples of which have been cited, as well as with the present suite of devices and methods.

FIG. 6a shows the distal end of the clamping catheter 70 with two rings of clamping balloons 71 and 72 in their deflated state, around the clamping catheter 70. The clamping catheter is of the appropriate length and diameter (greater than that of the delivery tube) for use in the application situation. The opening in the first tube is cut to fit the circumference of the stem of the graft core, not that of the larger clamping catheter. Thus pushing the clamping catheter through the smaller opening forces the wall to a larger circumference. When the clamp is removed the wall will return to the original unstretched size of the opening made for the stem. The clamping catheter 70 is made in sizes and shapes that duplicate those of guiding and diagnostic catheters and is advanced through a sheath using the same methods and skills as normally used in PCI procedures. The shapes have names such as Judkins, Amplatz, Arani, etc. These are designed for maneuvering in the femoral artery, aorta and coronary arteries. Application situations other than these served by present state of the PCI art will undoubtedly require other shapes and sizes. The preferred embodiment of the devices and methods of the invention disclosed here include such shapes for the clamping catheter as are in common use in PCI situations but do not include such shapes and sizes as may be required for all application situations. Whatever shape and size is selected, the clamping catheter is advanced through a natural or percutaneous entry to the site of anastomosis in first tube.

In FIG. 6a it may also be seen that the clamping catheter has a double wall 73 with a divider 74 between the halves of the crescent-shaped conduit made by the double wall. It should be noted that any conduits for carrying the liquid that inflates the clamping balloons must take up space either inside or outside the wall of a single wall catheter. That is, they cannot be coincident with the catheter wall. Because of the need to inflate the balloons quickly, this non-tubular conduit is designed to carry a larger volume than would two tubes that increase the diameter of the clamping catheter as much as does the double wall. An additional volume of fluid flows in the "wings' of the crescent. One half of this crescent-shaped conduit has an entry port to the distal balloon 71 and the other half an entry port to the proximal balloon 72. Neither port can be seen in this view. The end of the clamping catheter is open in this diagram in order to view what is inside.

FIG. 6b shows the distal clamping balloon 71 and proximal balloon 72 in their inflated state. Radiopaque markers 75 are on the balloons and on the distal end of the clamping catheter 70 for use in determining their location by fluoroscopic means. After the wall of the first tube has been cut, probably by a circular excision balloon, it must be immediately clamped. The proximal clamping balloon 72 may be inflated prior to cutting but the distal balloon must remain deflated in order to fit through the opening cut. The size of the Opening will be smaller than the circumference of the clamping catheter in order to fit the stem of the proximal graft core that will later be lodged in the opening. The wall of the first tube 1 goes between them but is not shown in order for the balloons to be seen.

FIG. 6c shows a cross-sectional view of one inflated clamping balloon. The curved member 76 is made of compliant material while the straight portions 77 are made of non-compliant material. The clamping balloons are not simply unshaped balloons but specially shaped so that they do not touch the opening directly but create a ring of pressure at some distance from the opening in the wall. The compliant material bulges around the balloon's circumference to squeeze the wall in proportion to the amount of inflation pressure. The pressure is adjusted to achieve the minimum balloon pressure that will control bleeding from the open cut and loss of fluid from the lumen of first tube. Once this is achieved the clamping catheter is ready to perform its role as a guiding catheter for all devices advanced through it. The cutting device is withdrawn.

FIG. 6d shows a cross-section of the deflated distal clamping balloon 71 in a semi-inflated state and a conceptual diagram of the cross section. The purpose of these diagrams is to show how the compliant 76 segment and the non-compliant straight sections are folded. The support section 77 is made of non-compliant material. It is important not to distort, collapse or injure the intimal layer or the native state of the tissue surrounding the opening or it will not join properly with the end of the graft. The support section keeps the circumference of the interface section a small distance away from the catheter to avoid clamping directly on the open end of tissue resting on the catheter. As pressure is increased in the balloon the support section unfolds in relatively straight surfaces between the fold lines while the compliant material of the interface section bulges out in proportion to the internal pressure. This provides the necessary control of the amount of clamping pressure being applied to the two sides of the wall of the first tube. The pressure must be sufficient to stop bleeding and to seal the opening to prevent leakage of fluid from the first tube without inducing spasms.

The circular excision device is most likely to be used to cut the opening at the first tube site. Though others could be used, the figures and words used to describe subsequent methods are consistent with an approach to the wall of the first tube at ninety degrees. No time should be lost in moving the clamping catheter 70 into the opening and inflating the clamping balloons 71, one on each side of the wall of the first tube to stop bleeding from the excision and to prevent escape of the tube's fluid through the new opening. The proximal balloon may be inflated before the cut is made so that the clamping catheter may be advanced immediately through the opening and up to the point where the proximal balloon prevents it from advancing further. At this point the distal balloon may be quickly inflated. Radiopaque markers on the clamping catheter and balloons provide another method of ensuring that the distal balloon ring is exterior to the wall and the proximal balloon interior to the wall.

FIG. 7 shows the distal end of the explorer guidewire 79. Said guidewire is steerable by a J-tip bent by the physician to the shape wanted for the situation. The curve allows the wire to be guided in the direction of the bend by rotating the guidewire slightly with a torque tool that slides over the proximal end of the guidewire. The tip also has screw threads 80 on it. This enables the physician to embed it in the second tube when the target area is located. The distal end of the explorer guidewire also has an opaque marker 81 along its length. This allows it to be seen in orthogonal views of the fluoroscopic display. Thus it can be maneuvered in three dimensions.

Finding the target area will be more difficult in some application situations. For these a target guidewire 82 can be advanced to the target area through the second tube 2. FIG. 8 shows a target guidewire 82 in the second tube 2, with its longitudinal opaque marker 83 lining up with the marker 81 on the explorer guidewire tip. This makes the longitudinal axes of the two tubes parallel as well as close as seen in the two orthogonal fluoroscopic views. The screw-threaded tip can now be twisted into the second tube at the target area. The delivery tube is advanced immediately to make the slit at the target, so the embedded tip does not have to remain in place for more than a few seconds. Improvements in fluoroscopic devices are in one of the faster growing fields, so orthogonal fluoroscopic images will be available in most well-equipped catheter laboratories. Another device can be used if fluoroscopic images are not adequate.

FIG. 9a shows the explorer guidewire 79 with its screw tip 80 as a transmitter and the target guidewire 82 with a receiver tip 84. The RF signal to the transmitter is sent through the wire of the explorer guidewire, thus requiring no added space. The connection from the receiver to a display may require two wires. In this case a dual guidewire would be used as there is adequate space for guidewires in the second tube. Signal strength increases as the distance between transmitter and receiver decreases and the display would show this to guide the transmitter and receiver until only the wall of the second tube separates them.

Since it is important for the slit to be aligned precisely on the longitudinal axis of the second tube, two transmitters and receivers in line may be used in more difficult situations. The same RF signal is used for the two transmitters and receivers but a time delay line is placed between the two so they are distinguishable in time. The circuit in the display is sensitive to the strength of signal between the transmitter-receiver pair that send and receive at the same time. Thus when each pair is separated only by the wall of the second tube they are in longitudinal alignment as well as in immediate proximity.

Figure 9B:
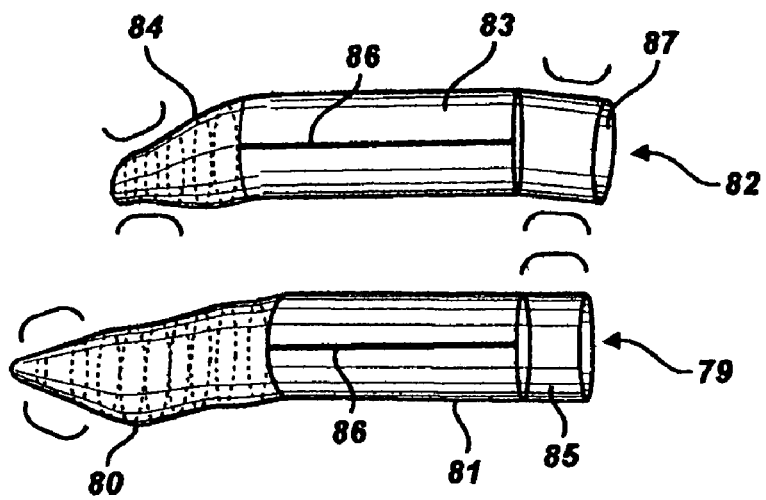
FIG. 9b shows a transmitter on the tip of the explorer guidewire and a delay line to a second transmitter proximal to the longitudinal marker and a target guidewire with two receivers and delay line between them.
Figure 9C:
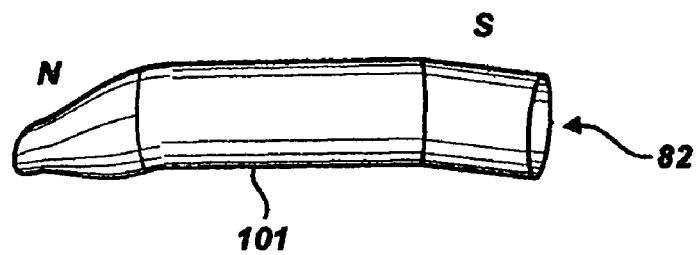
FIG. 9c shows two transmitters on the target guidewire and four receivers on the delivery tube.

FIG. 9b shows the locations of the two transmitters 80 and 85, with a time delay line 86 between them. Also shown are receivers 84 and 87 with the time delay line 88 between them. The opaque markers 81 and 83 are in white rather than black, as used in previous figures. FIG. 9c shows and south (S) and north (N) poles of electomagnet 101 in target guidewire 82. This is a magnetic alternative to two RF transmitters. The electro-magnet may have sufficient strength to draw the cutting blade toward it and keep the blade in place even with a beating heart. To increase the strength of attraction the blade may be magnetized as a permanent magnet. Care must be taken to mark its poles so they are appropriately aligned opposite the N and S poles in explorer guidewire 79.

FIG. 9d shows two transmitters 84 and 87 with delay line 86 between them mounted in the target guidewire 82 surrounded by four receivers 89, 90, 91 and 92 on the distal opening 93 of the delivery tube 10. This arrangement of transmitters and receivers is chosen for situations where the explorer guidewire does not provide sufficient accuracy for longitudinal alignment. The four receivers are shown on the delivery tube as it is advanced over the explorer guidewire to the target site. The receiver in the twelve o'clock position 89, is timed to receive the signal from the distal transmitter and the receiver in the 6 o'clock position 90, from the proximal transmitter. The receiver 91 in the 3 o'clock position and the receiver in the 6 o'clock position 92 are timed to receive first from one transmitter and then the other. The circuitry of receivers 91 and 92 compares the signal strength from each transmitter to determine when they are equal. They are then equidistant longitudinally. This circuitry also compares signal strength from each side to determine when they are equal to assure lateral equidistance. This circuitry is a variation of the century-old arrangement known as Wheatstone's bridge. When all comparisons are balanced the four receivers will be accurately positioned outside the graft and in line with its longitudinal axis. This arrangement need be taken only when necessary in a difficult application situation. Physicians who specialize in different application situations will quickly determine which devices and methods are appropriate for them.

The delivery tube 10 was advanced to the site of the clamping balloons with the explorer guidewire and remains there until the explorer guidewire has been screwed into the target. The delivery tube is then advanced to the target site. The delivery tube contains the graft with graft cores on each end. FIG. 10a shows a holding balloon 69 with a cutting device embedded that covers the opening in the distal end of delivery tube 10 as it follows along the explorer guidewire 79.

FIG. 10b shows the push-blade balloon 68 inflated and ready to cut at the site where the explorer guidewire is screwed in the second tube. The center opening in the holding balloon 69 is for withdrawing the cutting device after use. It also provides the exit notch for the explorer guidewire 79. When the explorer guidewire 79 was initially advanced toward the target site from the site of the clamping balloon 72 it was through this center opening.

When the end of the delivery tube is aligned with the graft at the target site the holding balloon is against and conforming with the outside wall of the second tube. If the cutting device mounted on the holding balloon is a tubular push-blade balloon, it is inflated and the slit made. If the cutting device is a tracked slitter no inflation is necessary, the wire controlling the blade is drawn, the slit is made and the blade sheathed. When a push-blade is used the balloon must be deflated to hide the blade before the delivery tube is advanced. Either cutting device may be withdrawn at this time or may be left in place as the delivery tube is advanced into the lumen of the second tube 2. Certain forms of cutting devices together with second tubes of small size create a danger to the wall opposite the opening if they are advanced without covering the blade by deflation. The cutting device and holding balloon are deflated and withdrawn outside the body after the anastomosis is made.

The length of the slit made is the length of the blade or the length of travel on the track. In either case this is determined by the circumference of the stem of the graft core. The length of the slit must be (approximately) one-half the circumference of the stem as each side of the slit fits around the stem. The circumference of the stem is 3.14 (pi) times the outside diameter of the stem. Thus the correct length of the slit is approximately one-half of 3.14 times the stem diameter. Dividing 3.14 by 2 yields 1.57. The cutting device selected should cut a slit that is about 1.57 times the diameter of the stem. This is just one of the approximate relationships among the dimensions of the devices.

A way of ensuring that the size relationships described in a later paragraph are maintained is for the manufacturer to assemble a correctly sized set of all the devices of this suite. The physician selects the correct suite based on the diameters of the first and second tube that are to be joined and the thickness of the graft. The physician has a choice regarding cutting devices and type of device for guiding the delivery tube. But once those sizes are determined prior to the operation, the sizing of the suite of devices is fixed and not a matter of preference.

After the slit is made, the delivery tube is immediately advanced through the slit opening and pushed downstream in the lumen of the second tube until it's heel is also in the lumen. Radiopaque markers on the heel and toe assist the physician in determining when the delivery tube's heel is inside the lumen.

Figure 10C:
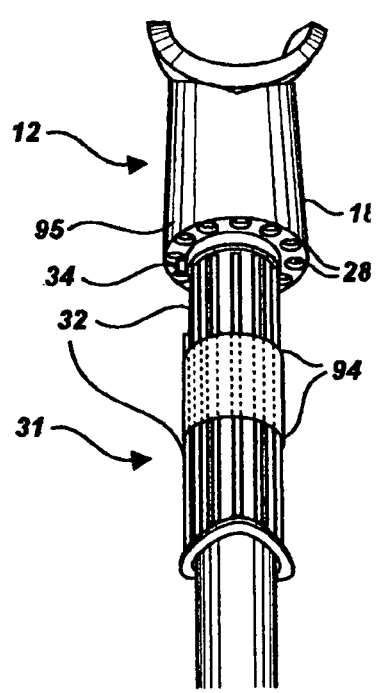
FIG. 10c shows a deflated rodding balloon close to entering the stem of the graft core.

Another catheter, with rodding balloon 31 at its distal end has been advanced through the delivery tube and into the distal graft core. FIG. 10c shows the rodding balloon 31 being advanced toward the base of the graft core 12. The hollow cones 28 are around the circumference of the base of the stem 18. Not shown are the stiff sutures 27 inside the stem 18, but the proximal end of each stiff suture is located at a hollow cone 28. This is the case with the embodiment illustrated. In an alternative embodiment the stiff sutures may be placed away from the hollow cones in the base by the distance that said stiff sutures travel a shorter distance than the stiff suture (s) that travel(s) the longest distance. In that embodiment the proximal rods would all be of the same length. In the illustrated embodiment, the rods 32 are shown with different lengths. The longest rod is for driving the stiff suture that travels the greatest distance to reach and enter the brim. The longest distance is at the point where the tangential angle is most obtuse, the 3 and 9 o'clock positions. Generally the more obtuse the tangential angle the longer the distance. The thickness of the graft is also a factor in this distance. Generally, the thicker the graft, the longer the distance. However these distances are computed by the manufacturer from tables given in a later paragraph. The differences in length shown are illustrative that there are differences and the ends of the rods form a pattern. The actual differences are computed as the distance of longest travel minus the difference of shortest travel. The longest rod touches its stiff suture(s) first and pushes it some distance before the second longest rods engage their stiff sutures, and so on. The longest rod has been driving its stiff suture(s) most of the distance to the brim when the shortest rod engages its stiff suture(s). The rodding balloon 31 is shown deflated. Since the balloon is deflated, the circumference of the circle the rods lie in is smaller than the circumference of the circle of hollow cones on the base of the stem. When the balloon is partially inflated the rods are still inside the graft core but the lip 94 of the balloon is expanded sufficiently be of a circumference to engage the base of the stem. This is for pushing against the base of the stem while the holding balloon is pulled against the brim to grip the core as the delivery tube is withdrawn. The rods are covered by a shaped cap so they do not catch on the anything. It does not expand when balloon inflates. A keyway 95 is shown on the interior of the stem. The key 34 is also shown attached to the rodding catheter. This key and keyway ensure that the rods engage the stiff sutures for which they were intended.

Figure 10D:
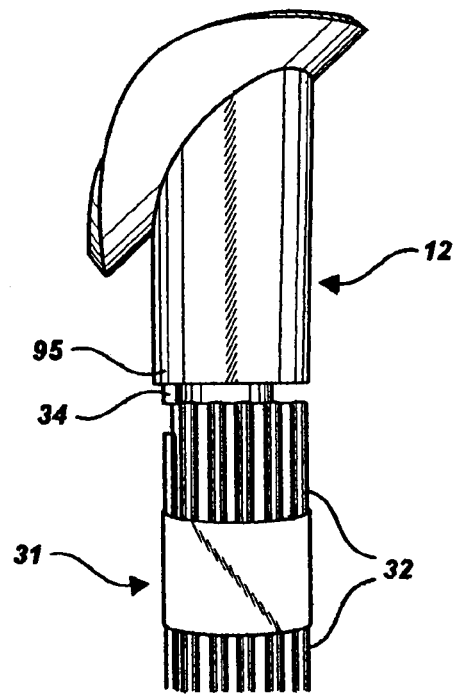
FIG. 10d shows a view of the inflated rodding entering the graft core with key and keyway aligned.

FIG. 10d shows the rodding balloon 31 inflated, making the twelve metal rods 32, in the same circumference as the stiff sutures and the stem in which they are located. The rods are seen being introduced to the stiff sutures located within the hollow sutures in the stem of the graft core 12. The part of the balloon that makes up the protective shells 94 is non-compliant material and thus does not move out with the rods when the balloon is inflated. The rods 32 are in place to push the stiff sutures 27. The relationship of key 34, shown in position in FIG. 4f and the keyway 95 shown in position in this figure as well as in detail are important at this point in the method. The keyway 95 and key 34 are used by the physician to determine when the rods are aligned with the hollow cone and when they are aligned on the base between the hollow cones 28. When the key is all the way counterclockwise in the keyway, the rods are in line with the hollow cones. When the key is turned clockwise to the other stop of the keyway the rods are between the hollow cones, i.e., ready to push against the base of the stem. The first action after introducing the delivery tube into the lumen of the second tube is to grip the graft core while the delivery tube is withdrawn. To do this the physician places the key in the clockwise position where the rods are aligned to the spaces between the hollow cones on the base of the stem.

The holding balloon is pulled by its wire while the rodding catheter is pushed, thus gripping the graft core between them. This brim of the graft core is inside the delivery tube and inside the lumen of the second tube. The stem of the graft core is in the delivery tube but extends outside the lumen of the second tube. The delivery tube is withdrawn outside the second tube and the brim 19, no longer compressed by the delivery tube, expands inside the lumen of the second tube 2. The brim deploys and is larger in circumference than the opening in the wall. The wall of the second tube 2 closes around the stem of the graft core.

The rodding balloon 31 is shifted to the counterclockwise position in the keyway and this brings the rods away from the base of the stem and into the hollow cones where they are in contact with the stiff sutures. To complete the anastomosis the stiff sutures are driven by the rodding balloon through the wall of the second tube and into the brim inside the lumen of the second tube, while the holding balloon is continually drawn proximally to hold the brim against the wall of the second tube. All stiff sutures are driven simultaneously to maintain balance around the circumference. To drive each separately would pull in the direction of each as it was driven. Another advantage of simultaneously driving the stiff sutures is that it requires only seconds to accomplish. Thus the conditions for a good graft are met and the stiff sutures are driven through the wall of the second tube and into the brim now inside the lumen of the graft. This completes the anastomosis of the second tube.

Figure 11A:
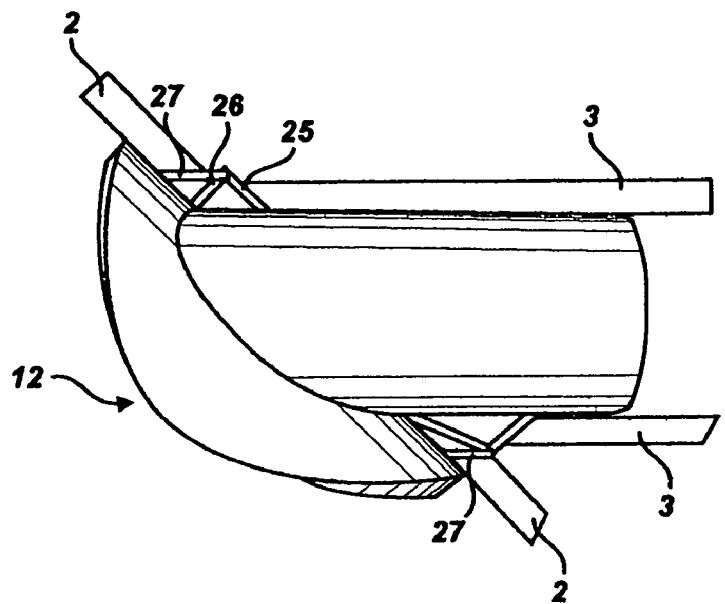
FIG. 11a shows the relationship of a cross-section of graft and wall of second tube with graft core, posts, hollow sutures and stiff sutures in a completed anastomosis.

FIG. 11a shows the graft core 12 with a graft 3 sutured on it (as was shown in FIG. 4c with the addition of a cross section of the wall of the second tube and the stiff suture pushed through said wall and into the brim. The hollow sutures 25 and posts 26 are shown holding the graft to the stem 18 of said graft core. Now the stiff sutures 27 are also shown cutting through the wall of the second tube 2 shown here in cross section. The wall of the second tube surrounds the stem along the junction and the angle of the wall approximates the miter as shown. That is, said wall's intimal layer pulls back more than the inner intimal layers after a slit is made along the longitudinal axis of the wall except at the 6 and 12 o'clock positions where the pull back is slight. However the pull back of the outer layer generally makes the inner layer closer to the junction creating a bevel of variable acuteness.

Figure 11B:
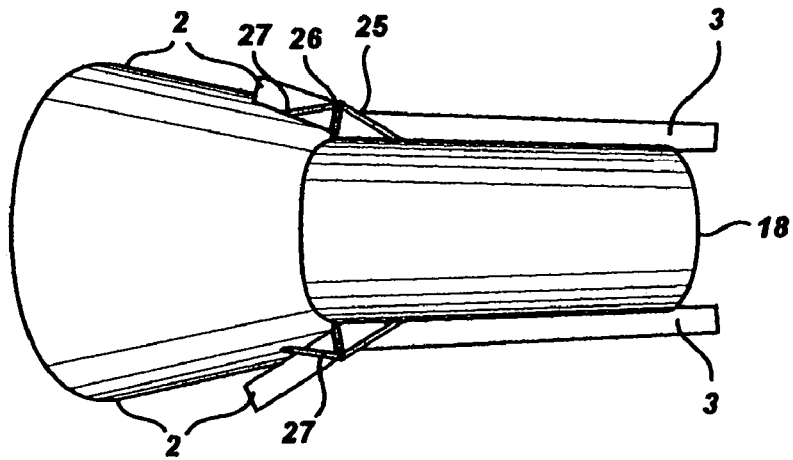
FIG. 11b shows the same anastomosis as shown in FIG. 10a from a different view.

FIG. 11*b* shows the same elements as FIG. 11*a* but at the 3 and 9 o'clock positions and with the inside surface of the tube also shown. If the outside surface were shown it would obscure the cross-sectional segment of the tube wall. The ghost of the brim is shown inside the tube. The stiff sutures are shown as having gone through the wall and lodged in the brim inside the lumen. After the anastomosis is thus finished with the second tube by driving the stiff sutures, the holding balloon is deflated and withdrawn with the cutting blade if it has not already been withdrawn. The rodding balloon remains as it will be used again in the anastomosis with the first tube.

A holding balloon of the same shape as holding balloon 69 is advanced on a thick guidewire to hold the brim of the proximal graft core in place for the anastomosis with the first tube. The same rodding balloon is used, but with the proximal side of the rods. The key 34 is set in the keyway 95 of the proximal graft core so the rods engage the stem when the rodding balloon is inflated. The clamping balloons on the first tube are deflated and the clamping catheter slightly withdrawn. The radiopaque markers on the delivery tube show when it is in a position where the brim is inside the lumen of the first tube and the stem in the opening. The rods are pulled against the stem of the graft core while the holding balloon is pushed, thus gripping the graft core while the delivery catheter is withdrawn. The key is then moved in the keyway so the rods are aligned with the stiff sutures and they are then driven through the wall of the first tube and into the brim being held in place by the holding balloon. This completes the second anastomosis and all devices are removed after deflation. The operation is finished with the conventional PCI closing procedures.

It is evident that there are relationships among the various devices of the present invention, particularly with respect to size. There are also infinities of possible angles and dimensions. For these and other reasons the suite of devices for a given application should be put together by the manufacturer licensed to manufacture and sell the devices when the physician defines the application situation. One of the ways of dealing with infinities of variables is that used with PCI devices such as catheters. Catheters are sized in production according to the French system. One French unit is one-third of a millimeter, three French units are one millimeter, 9 French is three millimeters and so on. The units are normally abbreviated as 1F, 2F, etc. This refers to inside diameters. Thus physicians order catheters by French sizes though there is obviously an infinity of possible sizes between the French sizes. The advantages of following the already established French convention is obvious. This in no way limits the dimensions of the present invention to French sizes. In addition there are relationships among the sizes of devices in the suite as described in this application for patent. The sizes vary with application situation but the relationships of sizes remains fairly constant. Using these relationships, as with using the French system of sizing reduces an infinity of possibilities to a meaningful manageable number. Without limiting the present invention to any particular sizes or relationships the sizes and relationships in Table 1 offer a practical way of managing an infinity of possibilities.

Table 1 gives typical sizes of the first tube and thickness of graft in coronary artery bypass application situations. These sizes would be determined prior to the operation and be used to select the proper size graft core and supporting suite of devices. In addition the physician would also determine the length of graft between the sites selected for anastomosis. The method the physician uses to make the measurements will affect the results. For instance a measurement made inside the lumen of the coronary artery will give a different result than a measurement made exterior to the same coronary artery at the same site. By either measurement the thickness of the coronary artery wall would have to be estimated to provide an estimate of the other dimension. Such estimating is expected and device sizes are sufficiently fungible to tolerate estimates. Likewise the relationships of device sizes are more rules-of-thumb than precise formulas. It is in this way that the values are given in Table 1. These, like the French system, give particular sizes, eliminating all in between. They also use particular (approximate) sizes of devices that all have appropriate dimensions for small body tubes. The relationships among the sizes as well as the sizes may be extrapolated to larger sizes. A column of figures in Table 1 represents the approximate sizes to be used together as a suite for one application. A new column of figures can be created by extrapolating from the numbers given in Table 1.

TABLE 1

| Tube OD | 3.6 | 3 | 2.4 | 2.1 | 1.5 |
|---|---|---|---|---|---|
| Brim OD | 2.8 | 2.4 | 2.1 | 1.5 | 1.2 |
| Brim ID | 2.1 | 1.8 | 1.5 | 1.2 | 0.9 |
| Stem OD | 2.1 | 1.8 | 1.5 | 1.2 | 0.9 |
| Stem Thick | 0.3 | 0.3 | 0.15 | 0.15 | 0.15 |
| Hollow Sut | 0.15 | 0.125 | 0.1 | 0.07 | 0.05 |
| Stiff Sut | 0.07 | 0.05 | 0.05 | 0.035 | 0.025 |

In Table 1 all entries are in millimeters. The Tube OD is the outside diameter of the smaller tube (usually the second tube) to be joined. Stem thickness is abbreviated Stem Thick and suture as Sut. The preferred embodiment of the present invention includes reasonable consistency in the relationships of sizes of the device in the suite.

Figure 12A:
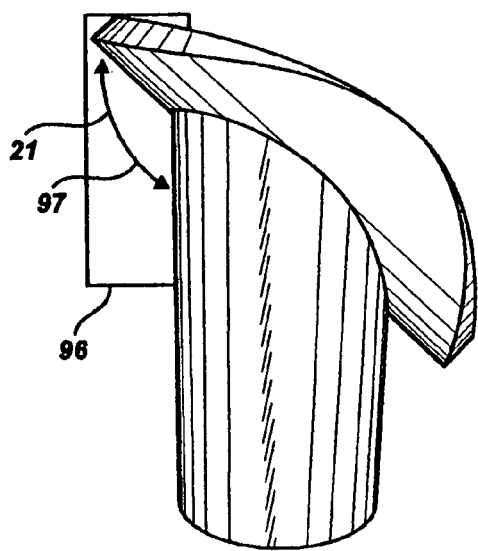
FIG. 12a shows a graft core and plane erected at 90 degrees to the tangent to the stem at the point of erection thus forming the tangential angle between stem and brim at that point.
Figure 12B:
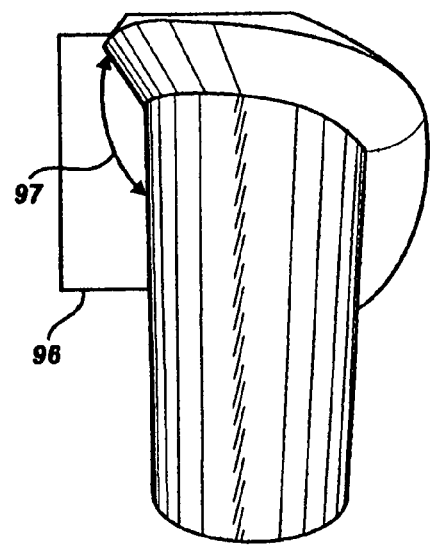
FIG. 12b shows the same erected plane tangent to another point on the stem and the tangential angle at that point.

Relationships regarding tangential angles, thickness of grafts and distance stiff sutures must travel are dealt with in the following figures. FIG. 12*a* shows a graft core where the longitudinal axes of stem and brim intersect at 45 degrees, producing an angle of intersection 21 of 45 degrees at the 6 o'clock position and 135 degrees at the 12 o'clock position. A plane 96 at right angles to the tangent at surface of said stem has been erected at the 12 o'clock position. This shows the tangential angle 97 of stem and brim at this position and it is the same as the angle of intersection at this position. It is also the same at the 6 o'clock position. But the angles of intersection are different at all other points on the junction. FIG. 12*b* shows the graft core rotated to the 2 o'clock position and a plane 96 erected at a right angle to the tangent at that point on the junction to show the tangential angle 97 of about 152 degrees at the 2 o'clock position. Half this angle is about 76 degrees for entry in the groove of cutting sleeve. It is larger than the tangential angle at 12 o'clock. FIG. 12*c* shows the tangential angle 97 at the 3 o'clock position. It is about 167 degrees and still more obtuse. It is evident that the greater the tangential angle the longer the distance the sutures must travel to reach the brim.

However the distance is also a function of the thickness of the graft. FIG. 12d shows a cross section of two grafts 98 and 99 on the same stem. This is for purposes of comparison as two grafts are never so placed in an application. The miter angle 100 is shown. Two hollow sutures and two stiff sutures are shown schematically because numbers on them would obscure their location. Each hollow suture comes out of the stem at 45 degrees toward the point of intersection of the miter flange and their graft. It is evident that the thicker the graft the farther the distance the stiff suture must travel to reach the brim. Without calculating all the possible distances, it is evident that they can be calculated. It is also evident that, like the French system for catheters, some conventions must be used to limit sizes from the infinite number of possibilities.

Although the present invention has been described with reference to preferred embodiments, workers skilled in the art will recognize that changes may be made in form and detail without departing from the spirit and scope of the invention.

What is claimed is:

1. A graft core device for drawing together two body tubes in an animal to make an end-to-side anastomosis, comprising,
   a. a stem section having a tubular shape and a wall with inner and outer circumferences, a circular planar base end, and an opposite end;
   b. a brim section having a tubular shape and a wall having inner and outer circumferences,
   c. said brim section attached to said stem section at a junction so that said sections form an angle,
   d. said brim section having a central opening,
   e. said brim section being made of material flexible enough to be compressed to a circumference slightly larger than the outer circumference of said stem section, but having sufficient shape memory to return to its original shape upon removal from compression,
   f. said stem section being made of relatively inflexible material having a plurality of segments of different types of suture material embedded in, and fastened to said stem section,
   g. a plurality of hollow suture segments having a tubular shape, made of relatively stiff, hard material, and longitudinally embedded in said wall of said stem section, starting close to said circular planar base end and proceeding longitudinally in said wall, emerging radially from said wall at an angle with respect to said stem section's longitudinal axis, and extending out from said wall and with ends pointed toward said brim section,
   h. a plurality of post segments of stretch-resistant suture material capable of returning to their original shape after bending,
   i. said plurality of post segments extending from near said junction of said brim and stem sections, radially aligned with, pointed in the direction of and of a length to intersect said ends of said plurality of hollow suture segments,
   j. said plurality of post segments further including means for forming respective connections to said plurality of hollow suture segments, thus creating a first plurality of closeable loops, each consisting of said post segment attached to said hollow suture segment and said wall of said stem section being the third side,
   k. a plurality of stiff suture segments constructed of stiff but bendable suture material,
   l. said stiff suture segments being slidably located inside said respective hollow suture segments but capable of being pushed out of said hollow suture segments, and
   m. said stiff sutures being sufficiently sharp to drive through body tissue and into said brim section, thus creating a second plurality of closable loops, each consisting of said stiff suture segment, said post segment, and said wall of said brim section being the third side,
   whereby (a) said stem section can be attached to an end of a first body tube by said first plurality of loops, (b) said brim section, while compressed, can be inserted in an opening made in the side of a second body tube and (c) when uncompressed expanding inside said second body tube to form a seal between said first and said second body tubes and (d) when attached to said wall of said second body tube by said second plurality of loops, (e) thereby holding said two body tubes in such contact as to create a more fluid-tight end-to-side anastomosis at said junction of said stem and brim sections of said graft core device than can a seal alone or sutures alone.

2. The device of claim 1, further including:
   a. a plurality of circular suture segments, constructed of stretch-resistant suture material and connected to said post segments so as to create a circumference of suture segments, said circular suture segments being attached or capable of being attached to said post segments where said post segments connect to said hollow suture segments, thus creating resistance to any force exerted to increase the circumference of said circular suture, including back pressure from said hollow suture segments connected to said post segments,
   b. a plurality of barbs on said plurality of stiff suture segments that fold flat against said stiff suture segments while being pushed out of said hollow suture segments but deploy outward when said stiff suture segments tend to move back into said hollow suture segments, thus preventing said stiff suture segments from backing into said hollow suture segments after being driven into said brim section and drawing said brim section into closer contact with said lumen of said body tube for a tighter seal between said brim section and said lumen of said body tube than exists before said barbs are lodged in said brim section,
   c. said plurality of hollow suture segments each having an end of conical or hemispheric shape and located in the base of said stem section where said plurality of hollow suture segments start, thus forming indents in said base capable of guiding a plurality of rod from another device into alignment with said stiff suture inside said hollow suture, and
   d. a shallow longitudinal groove on the interior of said stem section that acts as a keyway, allowing a protrusion on another device to enter as a key, thus aligning said stem section with said other device in a predetermined desired orientation.

3. The device of claim 1 wherein said graft core device is manufactured of a biodegradable material that will be absorbed by the body donor, has grown, said graft core device being coated with a pharmaceutical composition for promoting growth between said.

4. The device of claim 1 wherein said graft core device is made of biocompatible, non-biodegradable material that is joined to said graft, said graft being made of similar artificial biocompatible material such that said graft core device and said graft tube, being of non-biodegradable material, remain in the body permanently as a combination graft and graft core device and will provide the support functions of said post segments and said circular suture segments of said graft core device so that the only suture components attached or imbedded in said graft core of non-biodegradable material are said hollow suture segments and said stiff sutures segments that also are made of biocompatible, non-biodegradable material.

5. The device of claim 1 wherein said brim section of said graft core device extends outward from the outside of said stem section by a distance that is a function of the thickness of a wall of said graft tube and the tangential angle at which said brim section and said stem section meet at the points and where said posts emerge from said junction of said brim section and said stem section, said brim section having a plurality of small indents and ridges near the points where said stiff sutures enter said brim section, thus preventing said stiff sutures from skidding along the outer surface of said brim when being pushed into said brim.

6. The device of claim 1 wherein
   a. a first plurality of said stiff suture segments have sharp conical points,
   b. a second plurality of said stiff suture segments have a flat face and have been made sharp by truncating said second plurality of stiff suture segments at an angle to their longitudinal axis, thus creating a means of affecting the direction of travel of said second plurality of stiff suture segments toward the cutting edge and away from the flat face, and
   c. said flat face on said second plurality of stiff suture segments are placed in said hollow suture segments so as to drive said second plurality of stiff suture segments toward said brim section.

7. The device of claim 1 wherein each of said plurality of stiff suture segments is positioned in each of said plurality of hollow suture segments at a predetermined distance from each of said ends of said each of said plurality of hollow suture segments, the distance for each being based on a computation of the distance each stiff suture must travel from the end of said hollow suture to a target location on said brim.

8. The device of claim 1 wherein said stiff sutures are positioned in said plurality of hollow suture segments at said ends of said plurality of hollow suture segments.

9. The device of claim 1 wherein the outer surface of said brim section has a coating of a slippery substance.

10. The device of claim 1 further including biocompatible glue requiring the mixture of two parts for activation, one part being on said brim, and the other part being on the end of the stiff suture segment.

* * * * *